United States Patent [19]
Walker et al.

[11] Patent Number: 5,693,015
[45] Date of Patent: Dec. 2, 1997

[54] EXCHANGEABLE INTEGRATED-WIRE BALLOON CATHETER

[75] Inventors: Blair Walker, Long Beach; Manouchehr Miraki, Aliso Viejo; William Rice, Irvine; Kambiz Ghearzadeh, Costa Mesa; Brett Trauthen, Newport Beach; Hye Lee, Garden Grove; Greg Welsh, Newport Beach; Henry Nita, Mission Viejo; Shawn O'Leary, Newport Beach, all of Calif.

[73] Assignee: Advanced Cardiovascular Systems, Inc., Santa Clara, Calif.

[21] Appl. No.: 469,265

[22] Filed: Jun. 6, 1995

Related U.S. Application Data

[60] Division of Ser. No. 228,550, Apr. 15, 1994, Pat. No. 5,454,788, which is a continuation-in-part of Ser. No. 970,581, Oct. 22, 1992, Pat. No. 5,364,354, which is a continuation of Ser. No. 690,447, Apr. 24, 1991, abandoned.

[51] Int. Cl.$^6$ ............................................. A61M 29/00
[52] U.S. Cl. ............................. 604/96; 604/95; 604/280
[58] Field of Search ........................... 604/95, 280, 283, 604/159, 96; 128/656, 657, 658, 772

[56] References Cited

U.S. PATENT DOCUMENTS 5,190,529  3/1993  McCrory et al. ............... 604/280 X
5,242,430  9/1993  Arenas et al. ..................... 604/280
5,312,338  5/1994  Nelson et al. ........................ 604/95
5,325,868  7/1994  Kimmelstiel .................... 604/95 X Primary Examiner—John D. Yasko
Attorney, Agent, or Firm—Heller, Ehrman, White & McAuliffe

[57] ABSTRACT

A balloon catheter includes a flexible small-diameter guide wire provided with an enlarged-diameter distal end portion, and a flexible elongated tubular shaft with at least one dual-function fluid-conducting lumen adapted to both receive the guide wire extending therethrough, and to communicate pressurized inflation fluid to a distal balloon of the catheter. A distal orifice of the catheter communicates with the balloon and is provided with selective valving means for releasably engaging sealingly with the enlarged distal end portion of the guide wire. Apparatus is disclosed for axially moving the guide wire to effect engagement and disengagement of the enlarged distal end portion with the selective valving means of the catheter shaft. A torquer device is also provided by means of which the guide wire may be rotated relative to the catheter shaft for steering of the guide wire along a vascular pathway. A distal end tapered portion of the catheter shaft provides protection for a joint of the guide wire assembly. The tubular shaft of the catheter may extend through the balloon to provide better pushability for the catheter, especially in versions which employ a comparatively limp material for the balloon. Several alternative constructions for the selective valving means of the catheter shaft and for the enlarged distal end portion of the guide wire assembly are presented.

6 Claims, 15 Drawing Sheets

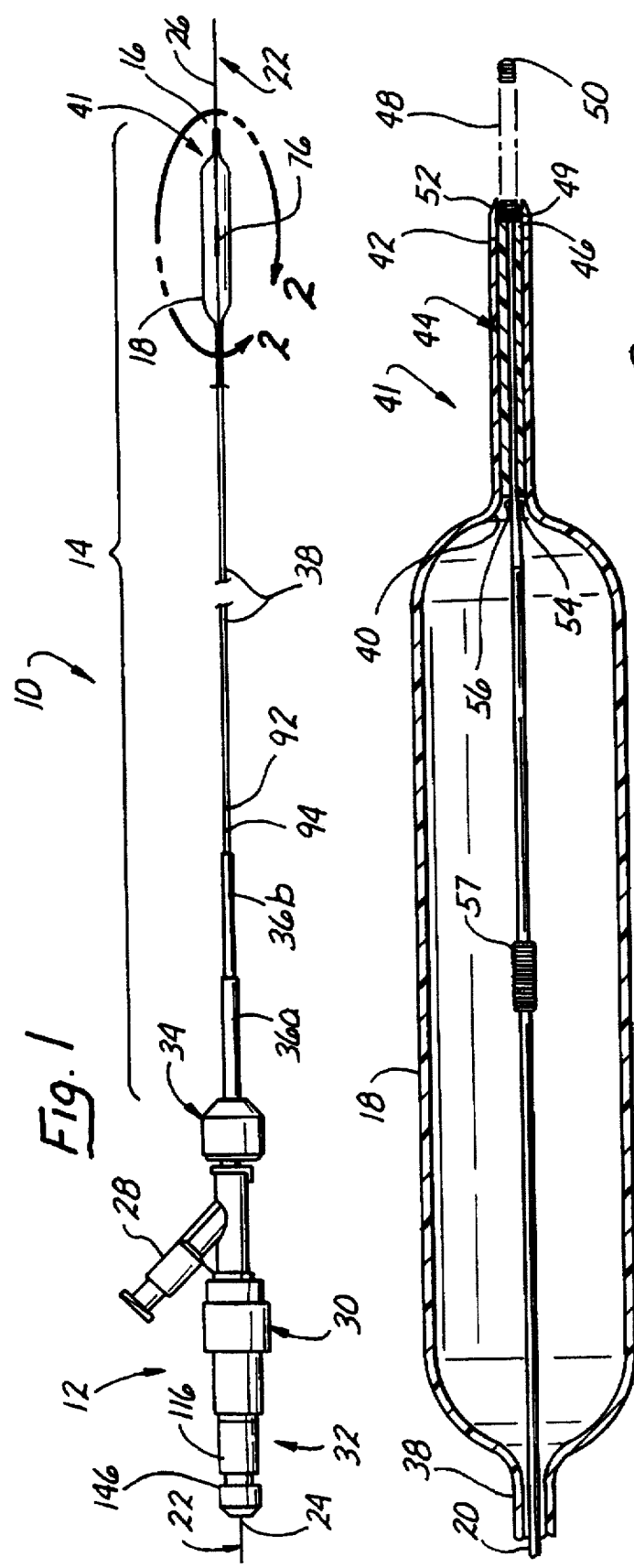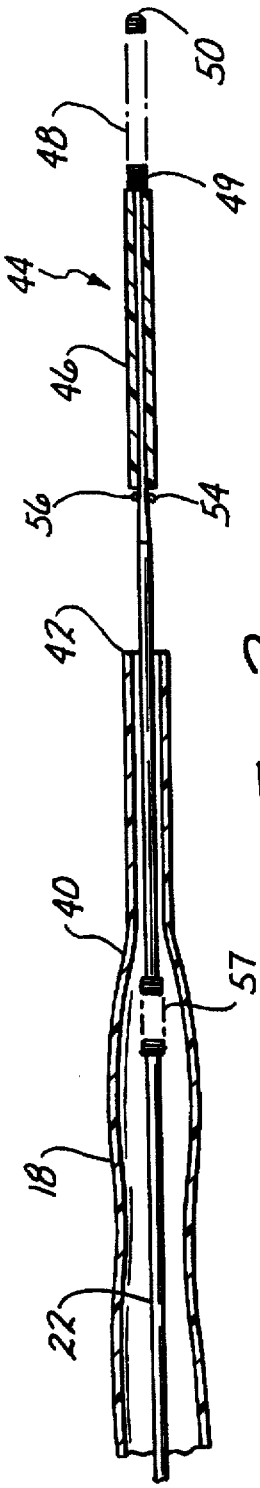

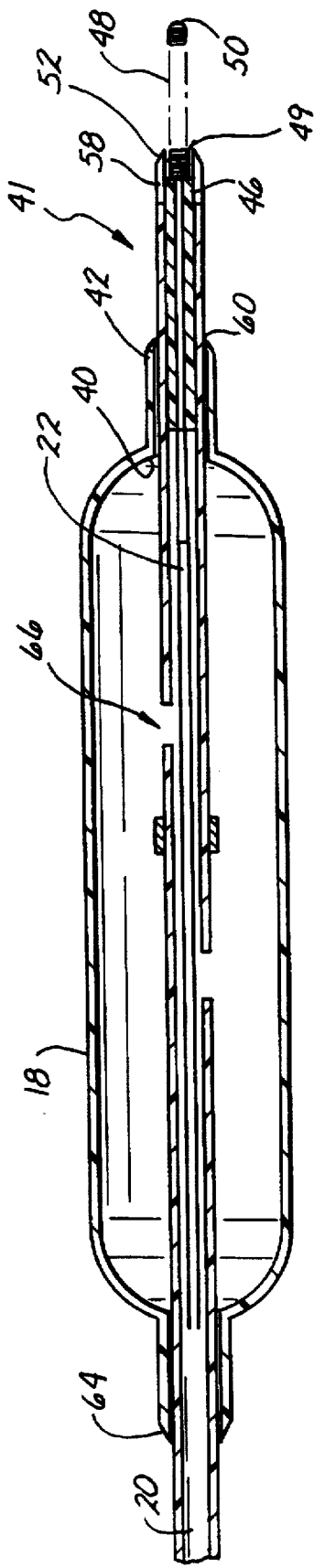
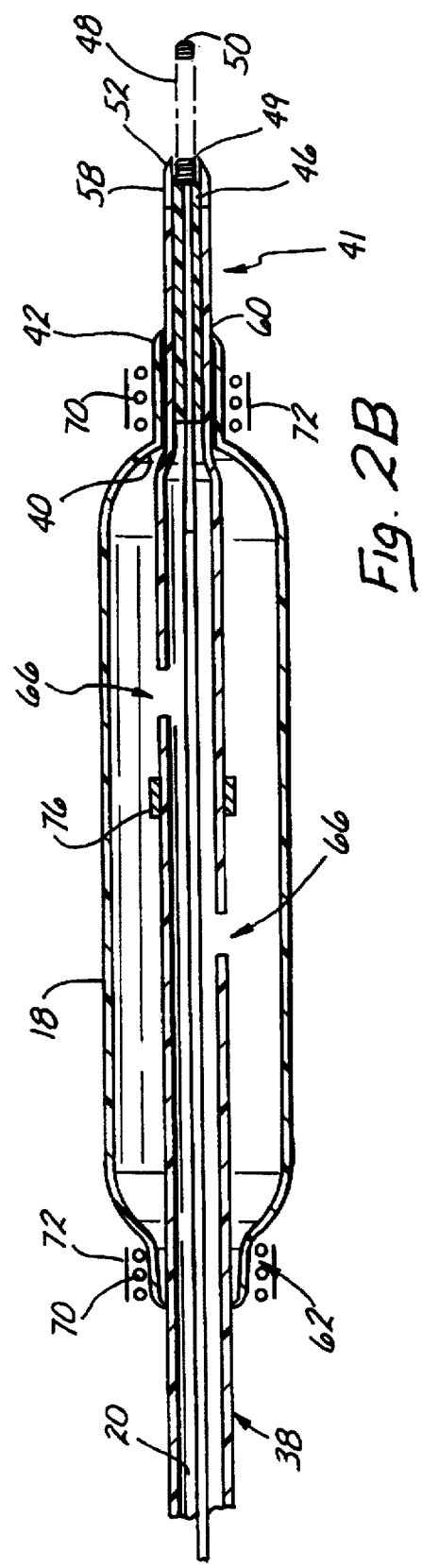
Fig. 2A
Fig. 2B

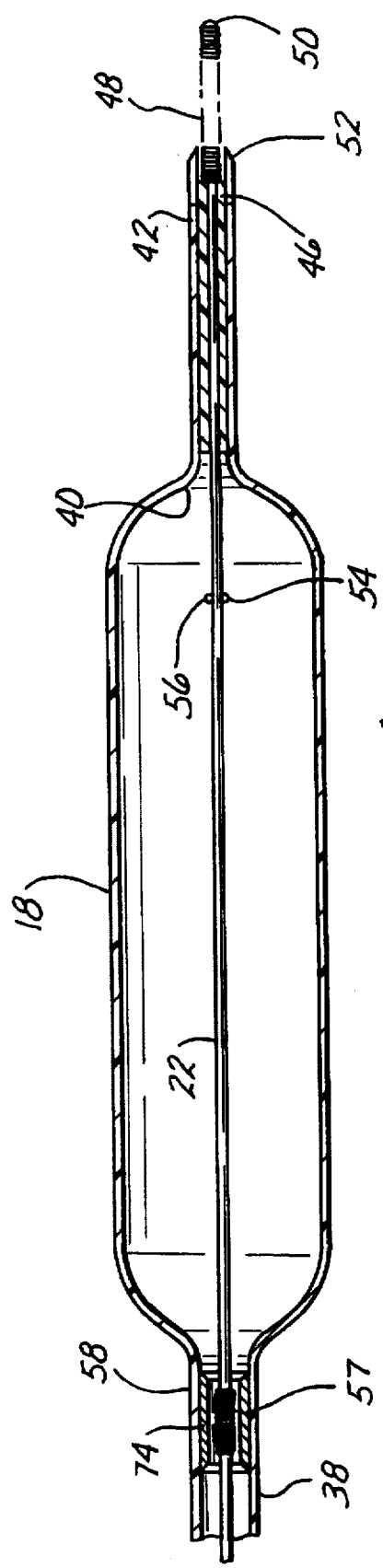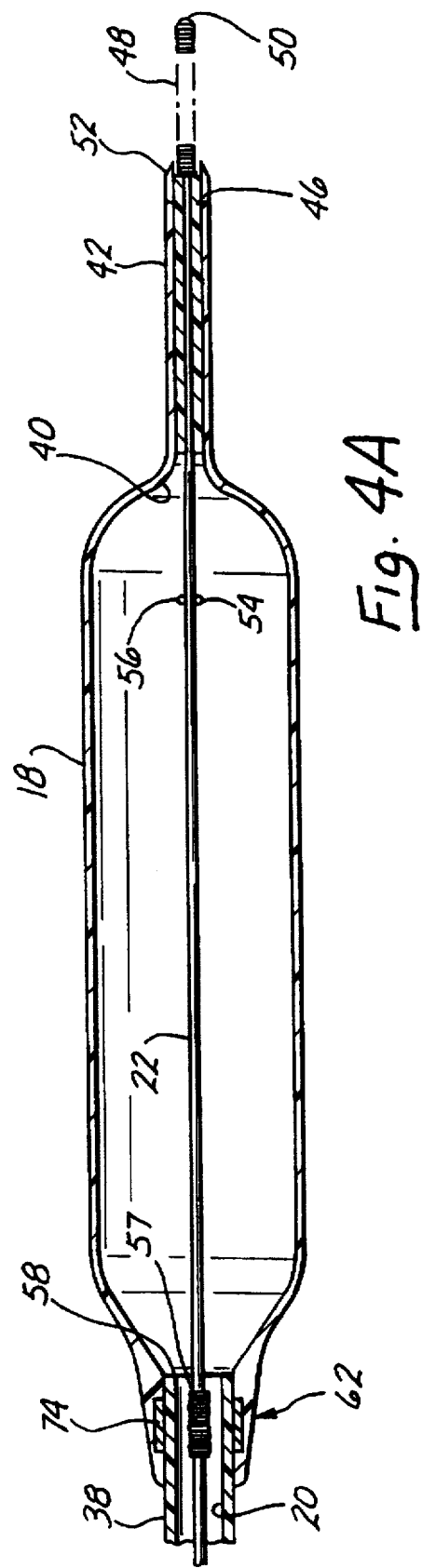
Fig. 4
Fig. 4A

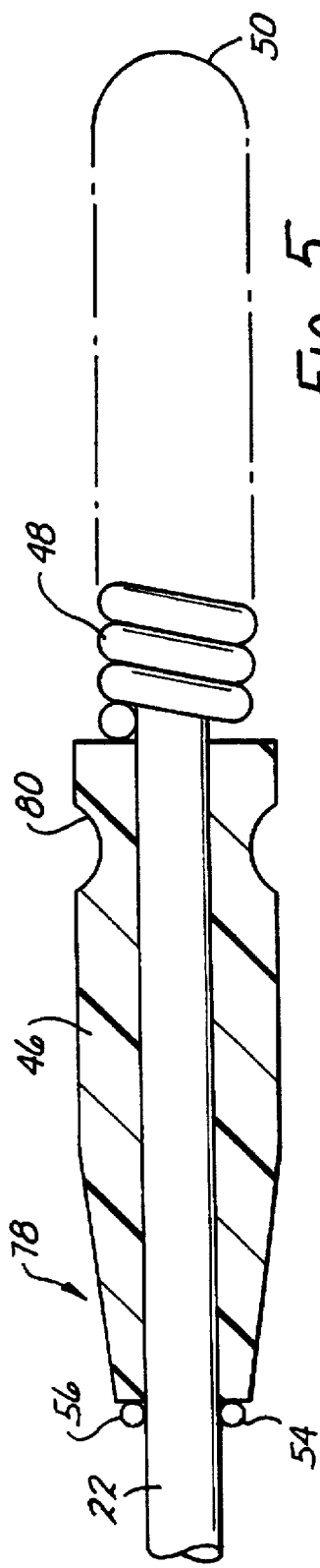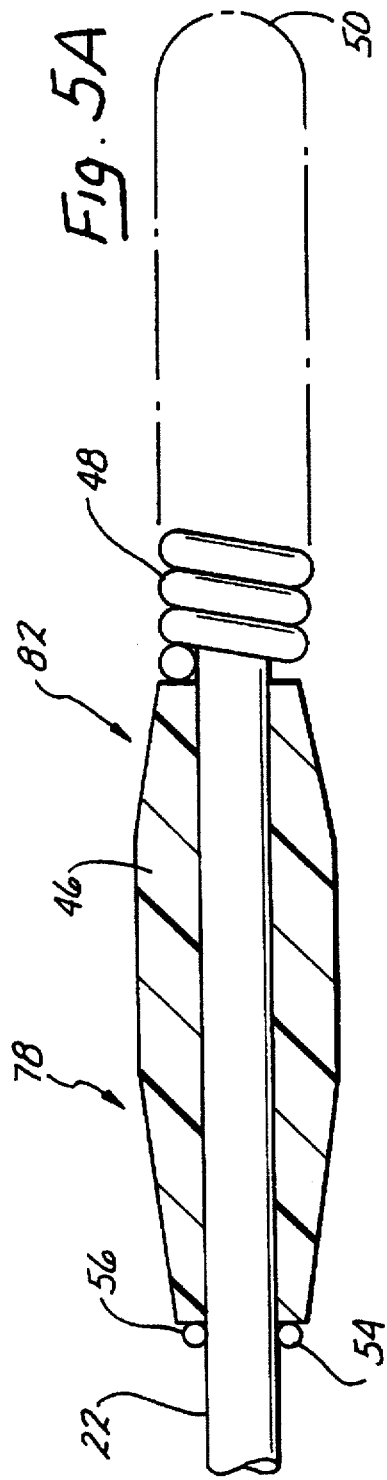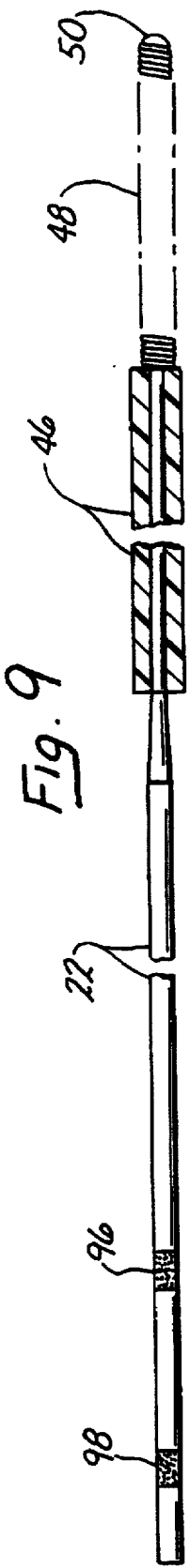

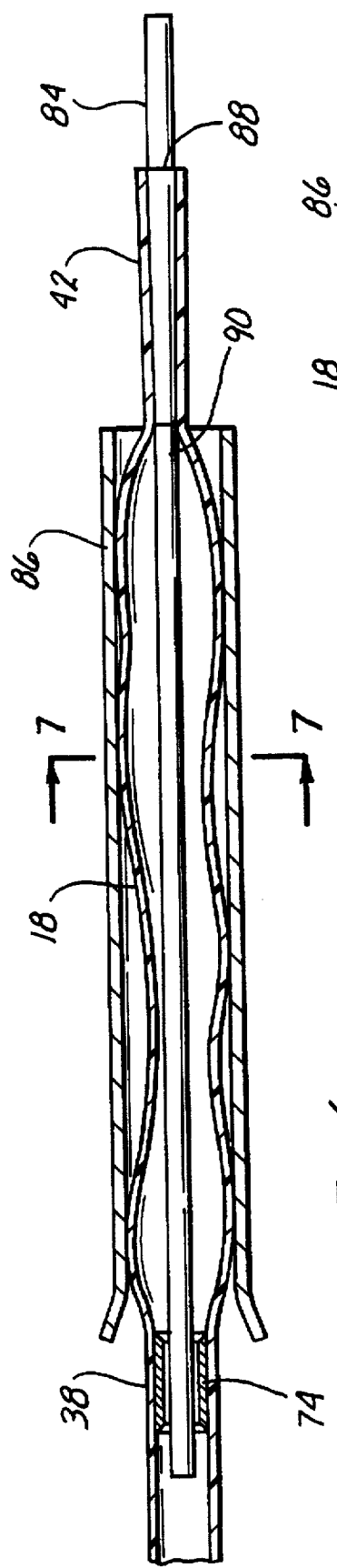
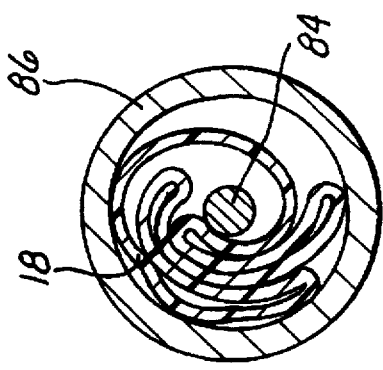
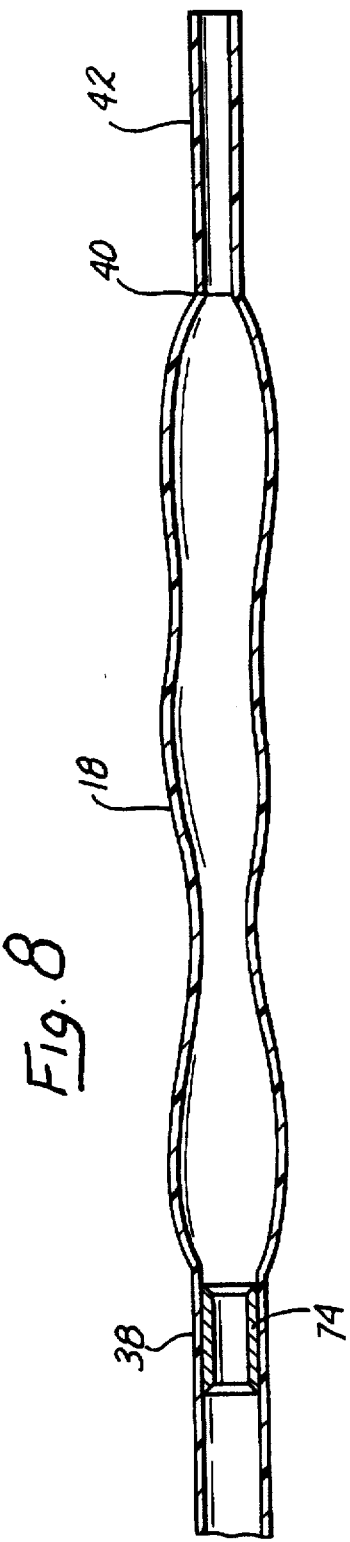

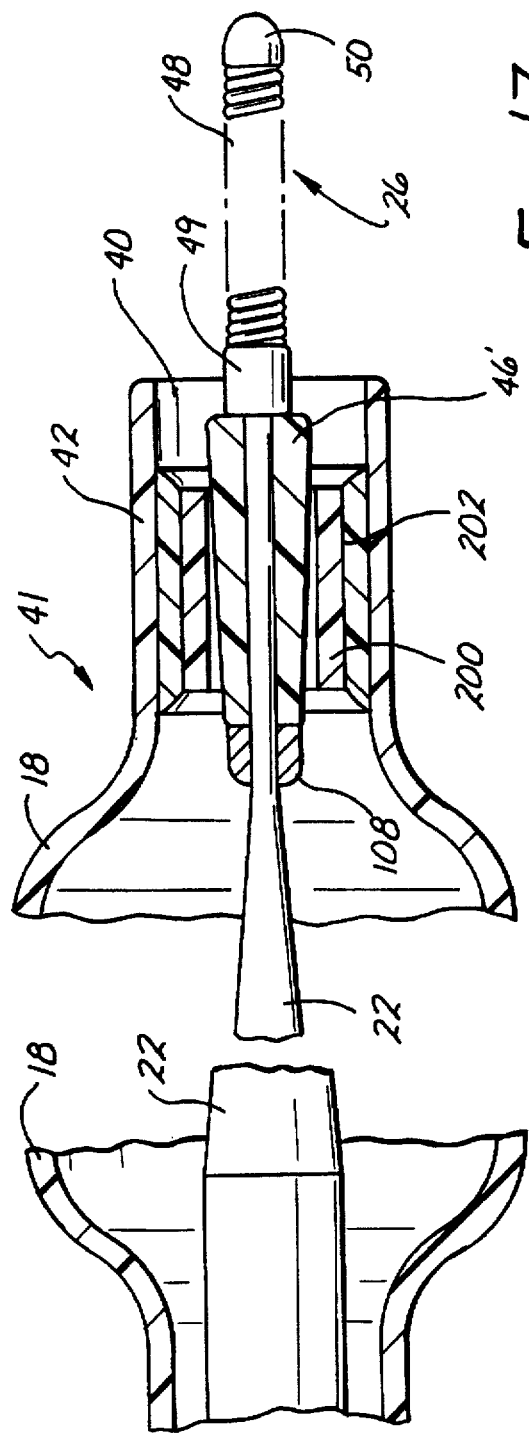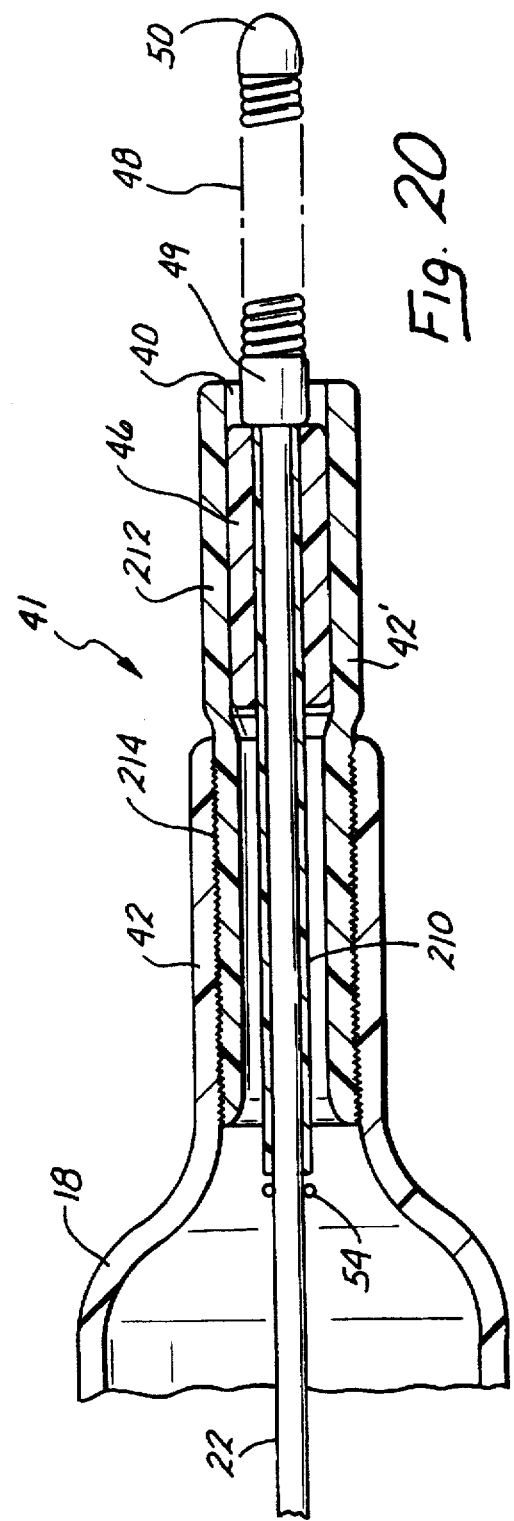

EXCHANGEABLE INTEGRATED-WIRE BALLOON CATHETER

RELATED APPLICATION

This is a division of application Ser. No. 08/228,550 filed on Apr. 15, 1994 now U.S. Pat. No. 5,454,788 which is a continuation-in-part of Ser. No. 07/970,581 filed Oct. 22, 1992 now U.S. Pat. No. 5,364,354 which is a continuation of Ser. No. 07/690,447 filed Apr. 24, 1991, now abandoned.

FIELD OF THE INVENTION

The present invention relates in general to the field of balloon catheters employed in the treatment of vascular diseases. More particularly, the present invention relates to a balloon catheter assembly which can be positioned quickly and easily for use in opening vascular stenoses, yet which also provides the additional advantage of providing for rapid balloon removal and replacement while retaining a guide wire in place across a treatment site to provide wire-guided access of a subsequent larger balloon catheter, for example, to the stenotic lesion.

BACKGROUND OF THE INVENTION

Over the last decade the medical procedure known as angioplasty has become widely accepted as a safe and effective method for treating various types of vascular diseases. For example, angioplasty is widely used for opening stenoses throughout the vascular system and particularly for opening stenoses in coronary arteries. At present, the most common form of coronary angioplasty is called percutaneous transluminal coronary angioplasty (PTCA). This procedure utilizes an elongate more or less flexible dilatation catheter having an inflatable balloon at its distal end. Using a fluoroscope and radiopaque dyes for visualization, a physician may steer the distal end of the dilatation catheter into position through a guide catheter and across the stenosis. Once so positioned, the dilatation balloon is inflated for a brief duration to open the artery and establish adequate blood flow.

Typically, inflation of the balloon is accomplished by supplying pressurized fluid through an inflation lumen in the catheter. This inflation lumen is connected to an inflation apparatus, which includes a source of pressurized inflation fluid and is located outside the patient's body. Conversely, applying a negative pressure to the inflation lumen collapses the balloon to its minimum dimension for removal of the balloon catheter from within the target blood vessel. Such an application of negative pressure to the dilatation balloon is also used to insure that the balloon has its minimal dimensions during insertion of the balloon to a treatment site.

In the past years a number of balloon catheter designs have been developed which have contributed to the safety and acceptability of PTCA and similar medical procedures. The most common design is known as an "over-the-wire" balloon catheter. This conventional dual-lumen device typically utilizes a relatively large lumen for passage of a guide wire and injection of angiographic visualization dye to assist in the placement of the device. A second parallel lumen is provided for inflation and deflation of the balloon. Typically, a steerable guide wire is positioned within the larger lumen and the entire assembly is maneuvered into an initial position within the target artery through a previously positioned guide catheter having an inner diameter of appropriately larger size sufficient to pass the treatment catheter. Once near the site of the stenoses, the guide wire can be rotated and axially extended or retracted into position across the lesion. The balloon dilatation catheter is subsequently advanced along the guide wire to position its deflated balloon across the lesion. Inflation of the balloon effects dilation of the stenosis.

Though successful at opening stenotic lesions, these dual-lumen catheters are relatively bulky and stiff, which makes their use difficult for any lesions except those that are proximal and localized in non-tortuous, easily accessible vessels. Moreover, these over-the-wire balloon catheters are of an early design, and require an additional implanting physician or assistant to control the guide wire during positioning of the assembly because movement of the catheter and guide wire are independent of one another. This complex coordinated activity requires both experience and skill, and may also result in a slower insertion procedure than is desired.

An alternative over-the-wire catheter assembly utilizes a non-removable guide wire that allows for longitudinal or axial movement. However, this design has a significant drawback because the entire non-removable guide wire catheter assembly must be removed to accomplish replacement or exchange of the balloon. In some cases of PTCA it is necessary to replace the balloon with one of different diameter or configuration following the initial dilation. Additionally, cases of acute re-closure have been noted where the lesion re-closes following dilation and removal of the balloon catheter. This alternative over-the-wire system adds to the difficulties of these subsequent procedures by requiring that the replacement catheter renegotiate the entire placement vascular path without the advantage of a retained guide wire position. That is, when the catheter is pulled out to allow a catheter exchange, the path to the treatment site is at least partially lost because the guide wire comes out with the catheter assembly.

Another version of conventional balloon dilatation catheters are known as, "mono-rail" variants of the standard balloon-on-a-wire system, and have been developed so that only a distal portion of the balloon catheter tracks over the guide wire. These mono-rail catheter systems utilize a conventional inflation lumen and a relatively short guiding or through lumen for the guide wire at the distal end of the catheter. The principal benefits of the mono-rail variant of balloon dilatation catheter is the reduction of frictional drag over the length of the guide wire, which is external of the catheter over much of the length of the catheter, and the ease of balloon exchange. The mono-rail catheters provide the ability to recross an acutely closed vessel or to exchange balloons without removing or extending the guide wire. However, a disadvantage of this design is the increased difficulty in steering the guide wire because this guide wire is not supported by the balloon catheter itself. Additionally, the mono-rail catheters are at least of dual lumen configuration at their distal ends, and this design produces a larger profile for the catheter and a larger shaft size.

Another conventional balloon dilatation catheter design is the "fixed-wire" or integrated "balloon-on-a-wire" dilatation catheter. These single-lumen designs utilize a relatively small guide wire diameter positioned within an inflation lumen and permanently fixed to the distal end of the dilatation balloon. This design produces a low-profile assembly which is able to cross severely narrowed lesions and to navigate tortuous vascular pathways. Additionally, the fixed guide wire is bonded at the distal end of the balloon, and improves the steerability and pushability of these designs. This aspect of the fixed-wire catheters also enhances their maneuverability. The thin shaft design of these catheters also improves coronary visualization, and enables all but the tightest critical lesions to be crossed. However, although able to provide relatively quick and simple balloon placement, as well as providing access to lesions otherwise unsuitable for PTCA, balloon-on-a-wire systems sacrifice both the ability to maintain guide wire position across the lesion when exchanging balloons, and also the safety advantage of being able to recross an acutely closed vessel without repositioning the entire assembly.

SUMMARY OF THE INVENTION

In view of the deficiencies of the conventional technology, it is an object for the present invention to provide a balloon-on-a-wire dilatation catheter which incorporates all of the benefits of a small diameter fixed-wire system yet allows for removal, reengagement or replacement of the balloon while leaving the guide wire in place to preserve an easily renegotiated path along the blood vessel being treated.

An additional object of the present invention is to provide an integrated-wire dilatation catheter offering an extremely low profile and a small shaft size to facilitate maneuverability and placement of the catheter as well as to provide the catheter with the ability to negotiate tortuous vessels and to pass highly stenosed lesions.

A further object of the present invention is to provide an integrated-wire balloon catheter having a steerable guide wire releasably fixed inside the catheter to provide enhanced torqueability, pushability, and maneuverability in order to facilitate the rapid, single operator placement and positioning of the catheter assembly.

Yet a further object of the present invention is to provide a balloon-on-a-wire dilatation catheter which allows for removal, reengagement or replacement of the guide wire while using the same catheter.

It is yet a further object of the present invention to provide an integrated-wire balloon catheter which meets the above-identified objects yet may be used in embolectomy applications for treatment of vascular lesions.

Another object for the present invention is to provide such a catheter assembly which includes an enlarged distal section of the guide wire forming in cooperation with a distal sleeve portion of the catheter shaft a valving device which may be selectively opened and closed by axial relative movement of the guide wire.

Still another object for the present invention is to provide in such a valved catheter assembly a radiopaque marker which serves the dual function of proximally positioning an inner sleeve member on the guide wire, which inner sleeve member serves to define the enlarged distal valving section of the guide wire, and of providing a feature which a physician may visualize with a fluoroscope to determine the opened or closed condition of the valving device.

Yet another object for the present invention is to provide such a catheter assembly in which the inner sleeve member on the guide wire distal end is formed on this guide wire in such a way as to essentially eliminate leakage of pressurized fluid at the interface of the wire and sleeve member and yet still allow relative rotation of this sleeve member on the wire.

Another object for the present invention is to provide such a catheter assembly also having a torquer assembly for grasping and twisting the guide wire so as to assist in steering this wire along a vascular pathway. The torquer assembly is especially configured to allow distal-end insertion of the guide wire into the catheter shaft by facilitating passage of the guide wire through the proximally-disposed torquer assembly.

Still another object for this invention is to provide such a catheter assembly also having a guide wire disengagement device located proximally of the catheter assembly and engageable with the guide wire for axially moving the guide wire relative to the catheter shaft in order to open and close the valving device at the distal balloon of the catheter.

These and other objects are achieved by the exchangeable integrated-wire balloon catheter of the present invention which, in accordance with broad structural aspects thereof, includes at least a single-lumen balloon catheter assembly having an outer sleevelike seal section adjacent to its distal end, which seal section releasably engages an enlarged distal end portion of a flexible guide wire running the length of the catheter assembly. This unique construction allows rotational and longitudinal movement of the guide wire relative to the balloon catheter where desired and, if necessary, allows the catheter to be removed and reengaged or fully exchanged over the guide wire. Further, additional lumens may be incorporated into the basic catheter design to carry drugs, blood, fluids and the like or to allow blood to passively perfuse the distal artery during balloon inflation.

More specifically, the flexible guide wire of the present invention is formed of metal, polymeric material or a combination of both and is provided with a relative small cross-sectional diameter to increase its flexibility and to reduce the overall cross-sectional profile of the dilatation catheter assembly. However, unlike conventional guide wire designs, the distal end portion of the present inventive guide wire steps up to an enlarged outer diameter.

The catheter assembly according to a first preferred embodiment of the present invention positions a small diameter proximal portion of the guide wire along the length of an axial lumen of an elongated tubular shaft of the balloon catheter and through the balloon itself. The expandable balloon portion of the catheter is connected to the distal end of the tubular shaft in a sealing or fluid conducting arrangement with the axial lumen. The distal end of the expandable balloon is provided with an orifice that is coaxially aligned with the axial lumen and adapted to receive or conduct the guide wire. The distal orifice in turn is provided with means for releasably engaging the enlarged diameter distal end portion of the guide wire in a sealing relationship to allow for pressurization and inflation of the balloon and to fix the wire within the catheter in order to facilitate maneuvering the assembly during placement.

In the catheter assembly according to a second preferred embodiment, the tubular shaft extends through the length of the balloon. The distal end of the tubular shaft in turn is provided with means for releasably engaging the enlarged diameter distal end portion of the guide wire in a sealing relationship, as specified for the first embodiment. The proximal end of the balloon is attached to the tubular shaft, and at least one slot is provided in the tubular shaft at about the mid-portion of the balloon to allow inflation fluid to be delivered from the axial lumen to inflate the balloon.

In this manner, the present invention combines the functions of fluid conducting and guide wire transmittal in a single lumen as opposed to the prior art dual-lumen balloon catheter designs. These unique constructions provide an exchangeable balloon catheter having an exceptionally small insertion profile and all of the advantages previously associated with non-exchangeable fixed-wire catheters; yet they also provide the advantage of the ability to leave the guide wire in position across a vascular lesion during balloon exchange or removal.

In the first preferred embodiment of the present invention the means for releasably engaging the enlarged diameter distal end portion of the guide wire in sealing relationship is a resilient sleeve which extends from the distal orifice of the expandable balloon. This sleeve is dimensioned to slide over and extend distally beyond the enlarged diameter distal end portion of the catheter as the catheter is advanced distally along the wire. Preferably, the distal portion of the wire is formed to have a smoothly surfaced, round cylindrical cross section as this construction allows the resilient sleeve to seal against the distal end portion of the guide wire. Additionally, it provides sufficient freedom of movement to allow the guide wire to rotate in place in order to facilitate the manipulation of the balloon catheter into position within a vascular pathway.

The means for releasably engaging the enlarged diameter distal end portion of the guide wire in sealing relationship according to the second preferred embodiment includes a resilient sleeve which extends from the distal end of the expandable balloon. This sleeve is attached to the distal end of the tubular shaft which is dimensioned to slide over and extend distally beyond the enlarged diameter distal end portion of the guide wire as the catheter is advanced distally along the wire.

Sliding the catheter proximally relative to the internal guide wire (or vice versa) slips the resilient sleeve off of the enlarged diameter distal end portion of the guide wire onto the smaller diameter proximal portion of the wire. The unseating of the resilient sleeve or the tubular shaft from the enlarged diameter distal end portion of the guide wire breaks the seal at the distal catheter end. In this position the guide wire can be advanced axially along the longitudinal axis of the catheter to cross narrow or irregular lesions or to follow a tortuous vascular pathway. Similarly, following dilatation the guide wire can be left in place across the stenotic lesion as the disengaged balloon is partially withdrawn along the wire to verify dilation of the stenosis, and restored blood flow.

If necessary, the balloon can be advanced again distally along the wire until the resilient sleeve or tubular shaft sealingly reengages the distal end portion of the guide wire. Following reengagement the balloon can be re-inflated. As those skilled in the art will appreciate, a complete exchange of the balloon is possible without loss of the track back to the treatment site utilizing the same general procedure along the positioned guide wire.

The embodiments according to the present invention may be adapted for use as an embolectomy catheter assembly, the only difference being that a balloon having a different material is provided in place of the flexible balloon typically used in angioplasty procedures.

To facilitate visualization of the guide wire and balloon catheter during the procedure, the apparatus of the present invention is preferably provided with one or more radiopaque markers. Typically, these markers are formed of small coils, strips or spheres of gold, platinum or other dense, relatively inert metal. In one embodiment of the present invention a radiopaque spring coil of flexible wire is provided distally to the enlarged diameter distal end portion of the guide wire. Similarly, in alternative embodiments of the present invention radiopaque markers are located along the guide wire at positions proximal to the enlarged distal end portion of the wire. It is also contemplated as being within the scope of the present invention to position radiopaque markers on the balloon catheter to enable the coronary physician to visualize the placement of the balloon relative to the guide wire and stenotic lesion.

Another version of the present inventive balloon catheter assembly includes a torquer located proximally of the catheter shaft and selectively engaging the guide wire for twisting this wire to effect steering of the guide wire along a vascular pathway. The torquer includes a feature particularly improving ease of guide wire passage through this torquer so that initial guide wire loading into the catheter assembly as well as catheter exchange over a positioned guide wire are improved.

The catheter assembly may also include a disengagement device engageable with the guide wire to effect axial movements of this guide wire relative to the catheter shaft. Thus, disengagement and reengagement of the enlarged distal valving sleeve with the outer sleevelike valving portion of the catheter shaft is facilitated by the disengagement device.

Also, the catheter assembly may include on the guide wire assembly, a valving sleeve member so formed as to be relatively rotational on the guide wire distal end portion, and yet which essentially offers zero leakage of pressurized fluid for balloon inflation at the interface of the sleeve member and guide wire. This essentially zero leakage aspect of the present invention may be important because the volume of an inflated dilatation or embolectomy balloon is not very great and the delivery of pressurized inflation fluid to these balloons is effected along a long narrow passage way or inflation lumen which may effect a significant pressure loss. Under these conditions, even a small loss of pressurized fluid at the valving device can adversely affect the forceful inflation effected at the balloon for therapeutic purposes.

Other features, objects, and advantages of the present invention will become apparent from a reading of the following detailed description, taken in conjunction with the accompanying drawing Figures which illustrate, merely by way of example, the principals of the present invention, and in which the same reference numeral refers to the same feature, or to features which are analogous in structure or function.

BRIEF DESCRIPTION OF THE DRAWINGS

FIG. 1 is a fragmentary elevation view of an integrated-wire dilatation catheter embodying the present invention;

FIG. 2 provides an enlarged cross-sectional view of an encircled distal portion of the balloon catheter seen in FIG. 1;

FIG. 2A is an enlarged cross-sectional view, similar to FIG. 2, of a distal portion of a second embodiment of a balloon catheter;

FIG. 2B provides an enlarged cross-sectional view, similar to FIGS. 2 and 2a, of the distal portion of yet another alternative embodiment of a balloon catheter;

FIG. 3 is a partial cross sectional view of a distal portion of the balloon catheter of FIGS. 1 and 2, and is shown in a collapsed or deflated operative position;

FIG. 4 presents a sectional view of the distal portion of an alternative embodiment of the present invention illustrating additional features thereof;

FIG. 4A is a sectional view of the distal portion of another alternative embodiment of the present invention illustrating additional features thereof;

FIG. 5 is an enlarged partial sectional view of an alternative embodiment of the distal portion of a guide wire usable in the balloon catheter of FIG. 1;

FIG. 5A is an enlarged partial sectional view of another alternative embodiment of the distal portion of a guide wire for the balloon catheter of FIG. 1;

FIG. 6 is an enlarged cross-sectional view of the distal end portion of a replacement balloon catheter illustrating additional features of the present invention;

FIG. 7 is a cross section of the balloon catheter of FIG. 6 taken along the line 7—7;

FIG. 8 is an enlarged sectional view of the replacement balloon catheter of FIG. 7 minus its packaging mandrel and cover;

FIG. 9 is a partial fragmentary view of an alternative guide wire illustrating additional features of the present invention;

FIGS. 17–26 depict fragmentary cross sectional views of alternative embodiments of the invention;

DETAILED DESCRIPTION OF THE EXEMPLARY EMBODIMENTS OF THE INVENTION

Figure 10:
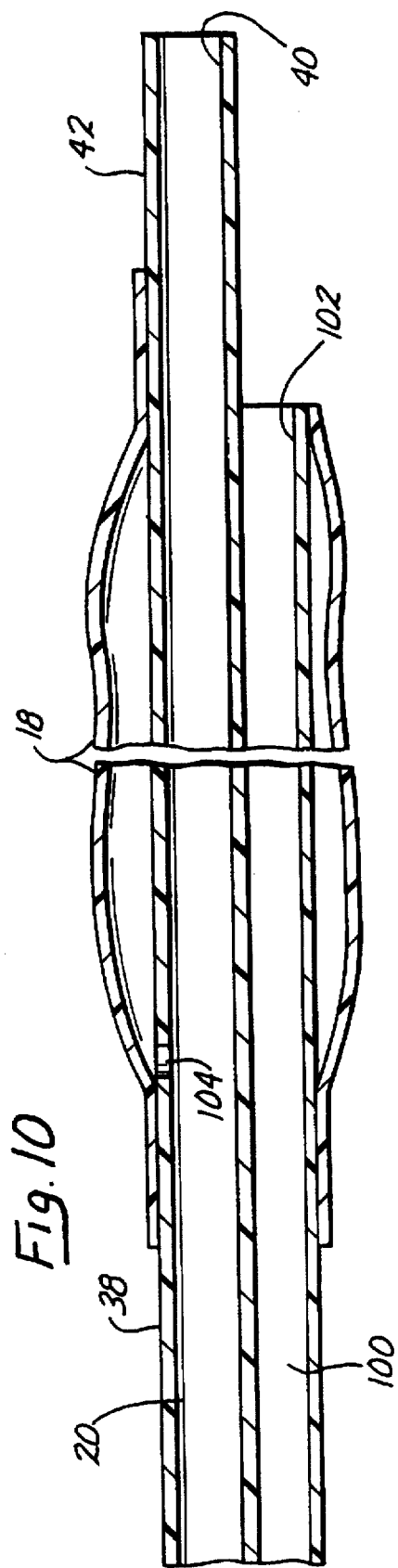
FIG. 10 is an enlarged cross-sectional view of the distal portion of an alternative dual-lumen balloon catheter illustrating additional features of the present invention.

Referring to the drawing Figures, FIG. 1 shows an elongate balloon catheter assembly, which is generally referenced with the numeral 10. The balloon catheter assembly 10 includes a proximal Y-connector, generally indicated by reference numeral 12. Catheter assembly 10 also includes an elongate tubular and flexible shaft portion 14, which terminates at a distal end 16. Adjacent to the distal end 16, the shaft portion 14 carries an expansible dilatation balloon 18. The catheter assembly 10 including Y-connector 12, is provided with a through passage or lumen (not seen in FIG. 1, but hereinafter generally referenced with the numeral 20) opening proximally on the Y-connector and distally at the distal end 16.

Through this lumen 20 passes an elongate guide wire assembly, generally referenced with the numeral 22. A proximal portion 24, and a distal portion 26, of the guide wire assembly 22 are seen extending from the Y-connector 12 and from the distal end 16, respectively, in FIG. 1. The guide wire assembly 22, as will be seen, is slidably movable through the lumen 20 of the catheter assembly 10, and is also removably engageable in a sealing relation with the catheter assembly 10 for purposes of inflating balloon 18. In order to effect the inflation of balloon 18, the catheter assembly 10 includes at Y-connector 12 an inflation port 28 which communicates with the balloon 18 via the lumen 20.

A hemostatic seal 30 is provided at the proximal end of the Y-connector to prevent fluid leakage around the guide wire 22. Preferably, the seal 30 is adjustable or releasable to facilitate the removal or exchange of the catheter assembly 10 from around the guide wire assembly 22, and also to facilitate removal of the guide wire 22 from within the catheter assembly 10.

Though not essential to the practice of the present invention, a torquer or drum 32 is associated with the Y-connector 12 and provides a physician with the ability to rotate the guide wire assembly relative to the catheter assembly. This rotation of the guide wire is manifest at the distal end portion 26, and may assist in steering the guide wire and catheter assembly 10 through a vascular pathway.

A compression or flare fitting 34 sealingly connects the shaft portion 14 of the catheter assembly 10 to the Y-connector 12. Distally from the fitting 34, the catheter assembly 10 may include also one or more strain relief members 36a, 36b, etc., sheathing the catheter shaft 14 over a portion of its length.

More particularly, viewing FIG. 1, the catheter assembly 10 includes an elongate tubular body 38 which is sealingly coupled to the Y-connector 12 in the fitting 34, and which alternatively extends either to the balloon 18, or to the distal end 16 while externally carrying balloon 18. Preferably, the tubular body 38 is formed of a polymeric material such as polyethylene, polyamide, polyimide, polypropylene, polyvinylchloride, polyester such as polyethyleneterephthalate (PET), or polyolefin copolymer. Additionally, body 38 may be coated with a fluoropolymer (such as PTFE), silicone or other materials including low friction lubricants. Alternatively, a proximal portion of the catheter shaft may be formed of fine-dimension metallic tubing (hypo tube). This hypo tube would be formed of stainless steel.

Adjacent to the distal end 16, the tubular body 38 of catheter shaft 14 carries the expansible dilatation balloon 18, which is shown inflated in FIG. 1. and the details of which are more readily apparent in the enlarged cross section of FIG. 2. As shown in FIG. 2, dilatation balloon 18 is formed as an integral part of catheter assembly 10 in fluid conducting communication with a single, axial lumen 20 running throughout the length of tubular body 38. Though the integral construction of catheter 10 illustrated may be preferred, alternative constructions may be utilized so long as dilatation balloon 18 is sealingly connected to the tubular body 38 adjacent to the distal end 16 of the catheter shaft assembly 14.

Accordingly, dilatation balloon 18 may be constructed of the same or different polymeric materials utilized in the construction of tubular body 38. Similarly, low friction coatings such as fluoropolymer (including, for example polytetrafluoroethylene (PTFE), generally known as "Teflon") or hydrophilic materials and lubricants (such as silicone) may be utilized to enhance the low-friction relative movements of all components of catheter assembly 10 during angioplasty or embolectomy.

Balloon 18 is provided with a distal orifice 40 which is coaxially aligned with lumen 20 and adapted to receive and conduct guide wire 22. As mentioned above, this guide wire 22 extends throughout the length of catheter assembly 10 including the balloon 18 and beyond distal end 16 via the distal orifice 40. Orifice 40 is provided with means for releasably engaging guide wire 22 in a sealing relationship. That is, the guide wire assembly 22 and catheter assembly 10 are configured cooperatively to define a valving device at the orifice 40, which valving device is generally referenced with the numeral 41, and which valving device 41 is responsive to relative axial movement of the catheter and guide wire assemblies to control fluid flow through the orifice 40. In the exemplary embodiment of the present invention, this means for releasably engaging in sealing relationship at orifice 40 (valving device 41) is formed of a resilient sleeve 42 which extends from distal orifice 40 and is dimensioned to slidingly engage an enlarged-diameter distal end valving portion (in the distal end portion 26) of the guide wire 22, which enlarged-diameter distal end valving portion is generally referenced with the numeral 44.

This enlarged distal end portion 44 includes a cylindrical collar 46 which is sealingly coupled to guide wire 22. Resilient sleeve 42 may be formed from the same material forming the remainder of tubular body 38 or may be formed from a lubricous polymeric material, or of other material. Alternatively, resilient sleeve 42 may be coated along its inner surface with a lubricous material to facilitate its engagement with cylindrical collar 46. Cylindrical collar 46 can be formed of a wide variety of materials ranging from stainless steel to polymeric materials and natural or synthetic gemstone, and may even be formed as an integral part of wire 22. However, it is preferred that collar 46 be formed of or coated with a polymeric material such as PVC, polyamide, polyimide, or fluoropolymer such as polytetrafluoroethylene (PTFE) as these materials provide an added degree of flexibility distal end portion of the guide wire which is formed by collar 46 and is of enlarged cross-sectional diameter. It is also preferred that the collar portion 46 may be formed of synthetic gemstone, with the sleeve portion 42 having a shape-conformal coating of elastic or resilient polymer on its inner surface for sealing cooperation with this gemstone valving member. An additional advantage of forming collar 46 from materials such as PTFE is that this cylindrical collar 46 may be sealingly coupled to guide wire 22 yet retain the ability to slide axially along guide wire 22, and to allow the guide wire 22 to be rotated inside the collar 46. When the collar member 46 is formed of gemstone, the surface of the collar member is highly polished, and rotational freedom of the guide wire assembly 22 is achieved simply by sliding this polished surface relative to the inner surface of the sleeve 42, while still maintaining a sealing engagement therewith.

Though not essential to the practice of the present invention, guide wire 22 is preferably provided with a flexible spring coil 48 positioned distally to the enlarged diameter cylindrical collar 46. The spring coil 48 is joined to the guide wire assembly 22 by means of a metallic braze 49, such as soldering or brazing. As shown in FIGS. 2–5, spring coil 48 is preferably provided with a smooth hemispherical tip 50 in order to reduce vascular trauma as guide wire 22 is advanced along a vascular pathway. Spring coil 48 may be formed of any resilient material, preferably metal, and in the preferred embodiment of the present invention is formed of a radiopaque material such as platinum or gold. Thus, spring coil 48 functions as an additional marker to assist the coronary physician in positioning the apparatus of the present invention.

For example, when spring coil 48 has been advanced to a position just beyond the target lesion the physician may be comfortable in knowing that balloon 18 is properly positioned across the lesion. At that point, as long as resilient sleeve 42 is sealingly engaging cylindrical collar 46, then balloon 18 may be inflated by pumping a pressurized fluid, such as saline or contrast medium, into inflation port 28 and along axial lumen 20. Following dilation of the stenosis, a negative pressure can be applied to port 28 and axial lumen 20 to delate balloon 18 prior to its removal from the lesion.

Though spring coil 48 is illustrated in FIGS. 2–5 as being relatively straight, it is commonly known in the art to pre-curve spring coil 48 so that the implanting physician can rotate wire 22 and direct tip 50 of wire coil 48 into specific vascular junctions to direct the entire catheter assembly 10 along a selected vascular pathway. Rotational manipulation of wire 22, or "torquing" as it is referred to in the art, is accomplished by rotating torquer 32 of Y-connector 12. As will be further explained, this torquer firmly clamps wire 22. The axially resilient construction of guide wire 22 transmits this torque along the entire longitudinal extent of wire 22 to coil 48.

However, because cylindrical collar 46 is preferably sealingly coupled to guide wire 22 in a rotatable manner, this torque is not transmitted to balloon 18 and prevents this balloon from wrapping in a spiral fashion around guide wire 22. Alternatively, where cylindrical collar 46 is not rotationally free relative to the wire 22, it is preferred that the outer surface of this cylindrical collar 46 be very smooth to allow a certain degree of slippage between it and the inner surface of the resilient sleeve 42. In this manner, balloon wrapping also can be prevented.

In this depicted embodiment of the present invention the cylindrical collar 46 is coupled to the guide wire 22 by using one of several methods. In a first method, a pre-extruded teflon tube of selected diameter representing the collar 46 is slid in a proximal direction over the guide wire 22 and beyond the distal tip 50. The coil 48 is then brazed to the distal tip of the guide wire 22 to keep the collar 46 in place. In a second method, a piece of teflon shrink tubing representing the collar 46 is slid over the guide wire 22 and the coil 48 attached to the tip of the guide wire 22. The collar 46 is then slid in a distal direction over the joint and the tubing is heated to shrink the teflon tubing against the guide wire 22.

Referring to FIG. 2, the cylindrical collar 46 is preferably located inside the resilient sleeve 42 so that the sleeve 42 extends distally beyond the collar 46 by about 0.005 to 0.025 inches. This configuration provides a stress relief because the transition between the collar 46 and the flexible spring coil 48 is protected inside the sleeve 42. This stress relief feature minimizes any kinking of the guide wire 22 at this transition. The sleeve 42 is externally buffed to produce a chamfer or taper 52 (by, for example, grinding) to create a smooth transitional tapered surface to aid in the atraumatic tracking of the selected vessel.

As shown in FIG. 2, to retain polymeric cylindrical collar 46 in position along guide wire 22, one or more retaining beads 54 and 56 may be soldered or brazed to guide wire 22. Alternatively, adhesives or a simple mechanical fit (i.e., an interference fit of the beads on the wire 22) may be utilized to retain the axial position of the collar 46 on the wire 22. It should also be noted that guide wire 22 and specifically cylindrical collar 46, may be formed from a lubricous polymeric material or provided with a thin coating of silicone, fluoropolymer or the like to increase its lubricity. This exemplary construction produces a releasably engaging seal which fixes guide wire 22 in position relative to balloon 18 yet allows guide wire 22 to be rotated freely without wrapping balloon 18 about the shaft of guide wire 22. Carried on the guide wire 22 and centered in the balloon 18 when the collar 46 is centered in the sleeve 42 to close the orifice 40, is a coil of radiopaque wire wrapping 57. This coil 57 serves as a marker for the physician who can center this marker at a stenosis to be dilated prior to inflating the balloon 18, as is further explained below with respect to the uses of this and other markers of the various catheter assembly embodiments.

In FIG. 3, balloon 18 has been deflated and retracted proximally along guide wire 22 to a position where resilient sleeve 42 has completely disengaged from cylindrical collar 46. It is important to note that, as shown in FIGS. 2 and 3, all portions of guide wire 22 proximal to its enlarged diameter distal end portion (formed by cylindrical collar 46) have a cross-sectional diameter smaller than that of the outer diameter of collar 46. This construction allows the balloon catheter of the present invention to be completely advanced or retracted along the entire longitudinal extent of guide wire 22 for the purposes of balloon manipulation, removal or replacement.

Thus, the balloon catheter can be replaced with a catheter having a balloon provided with a different expandable diameter if necessary to reopen a particularly difficult stenotic lesion. Similarly, if problems develop with the inflation of balloon 18 during angioplasty it is possible to replace the balloon with a properly functioning device. All the vascular physician need do is to retract tubular body 38 and balloon 18 along guide wire 22 leaving guide wire 22 in position across the target lesion. Then, a replacement balloon can be advanced along the positioned guide wire without having to retrace the entire vascular pathway.

As those skilled in art will appreciate, this greatly facilitates the speed and safety of such a procedure. In order to reengage the balloon on collar 46 the vascular physician simply advances the catheter along guide wire 22 to slide resilient sleeve 42 over cylindrical collar 46. Generally, in practice, when easy advancement of resilient sleeve 42 relative to collar 46 ceases, the physician can be sure that a sealing engagement between collar 46 and sleeve 42 has been achieved. The physician need not achieve full or relatively centered positional relationship of the sleeve 42 and collar 46 as is shown in FIG. 2. Generally, it is sufficient merely that the physician feel the frictional engagement of the collar into the sleeve. The complete engagement shown in FIG. 2 is for purposes of illustration only.

An alternative exemplary embodiment of the inventive catheter assembly is shown in FIG. 2A. In order to obtain reference numerals for use in describing the structure of this alternative embodiment, features which are the same or are analogous in structure or function to those depicted and described above, are referenced with the same numeral used previously. Viewing FIG. 2A, the distal end 58 of the tubular body 38 extends from the proximal end of the balloon 18 also through the length of the balloon, and distally of this balloon structure to define an equivalent to the resilient sleeve 42.

The tubular body 38 is bonded to the balloon 18 at a distal bond 60, and to the proximal end 62 of the balloon 18 at a proximal bond 64. The bonding is achieved by heat or adhesive bonding. In this embodiment, it is the distal end 58 of the tubular body 38 that is dimensioned to slidingly engage the cylindrical collar 46. The distal end 58 and the tubular body 38 are preferably made from a flexible material, preferably polyethylene. Alternatively, other materials and plastics may be used for the distal end 58, but the proximal end of the tubular body can be formed of metallic hypo-tube bonded to a distal end polymeric portion of the tubular body 38 in order to provide optimal pushability for the catheter assembly 10. The distal end 58 of the tubular body 38 extends beyond the collar 46 so that the collar 46 is located within the distal extension of this tubular body. Again, this proximal recessing of the collar 46 protects the transition between the guide wire 22 and the coil 48 from kinking. A taper 52 is provided at distal end 58.

Since the tubular body 38 extends the length of the balloon 18, the axial lumen 20 of the body 38 likewise extends across the length of the balloon 18 and terminates at the sleeve 42. Tubular body 38 is provided with one or more inflation slots 66 cut about 90–180 degrees apart from each other, and through which inflation fluid may be injected into the balloon 18. The slots 66 are preferably cut in the tubular body 38 at the mid-portion of the balloon 18 to facilitate uniform expansion of this balloon. Also, any number of inflation slots 66 may be provided without departing from the spirit and the scope of the present invention. If one inflation slot 66 is used, it is also possible to extend the length of the slot 66 across the length of the balloon 18 from the proximal bond 64 to the distal bond 60.

Thus, extending the tubular body 38 through the balloon 18 to form the sleeve feature 42 improves the manufacturability of the balloon catheter assembly 10, and also improves its performance during use by easing the engagement and disengagement of the guide wire 22. Further, the double bonding provided by the proximal and distal bonds 64 and 60 supports the balloon 18 from disengaging during balloon inflation, and supports the balloon structure during catheter exchange.

Referring to FIG. 2B, another alternative embodiment of the present inventive catheter assembly is illustrated. Again, in order to obtain reference numerals for use in describing the depicted structure, features which are the same or analogous in structure or function to features depicted and described above are referenced with the same numeral used above. In the embodiment of the invention depicted in FIG. 2B, the tubular body 38 is enlarged proximal of the point 68. That is, at the point 68, the tubular body 38 is necked down to distally of the point 68 define the sleeve feature 42. Such proximal enlargement of the diameter of the tubular body 38 relative to its distal size allows for smoother and easier guide wire and catheter exchange.

While the balloon catheter assembly of the present invention has been described above in connection with a dilatation catheter, an embolectomy balloon catheter assembly may also be provided in accordance with the above description without departing from the spirit and scope thereof. The embolectomy balloon catheter assembly is preferably made in accordance with the embodiment of FIG. 2A, with two modifications or requirements. First, the balloon 18 is made from latex, kraton or silicone instead of from a polymeric material. Second, the distal and proximal bonds 60 and 64 are preferably bonded by adhesive bonding, heat bonding or other conventional means. Also, for an embolectomy catheter having a latex balloon, it is preferable to provide thread, and preferably dacron, windings 70 around the distal and proximal bonds 60 and 64, with a urethane coating 72 applied over the windings 70.

Additionally, as shown in the alternative embodiment of the present invention illustrated in FIG. 4, the retaining beads 54 and 56 may be soldered to the guide wire 22 somewhat proximally to the distal location of cylindrical collar 46. The collar 46 is thus provided with an added degree of sliding axial movement along guide wire 22. This added axial movement for the collar 46 on the guide wire 22 allows the positioning physician to extend or retract the distal end portion 26 of the guide wire relative to the balloon 18 where necessary while still retaining the seal between collar 46 and sleeve 42. It should be noted that retaining beads 54 and 56 create an outer diameter which is larger than the inner diameter of cylindrical collar 46 yet smaller than the outer diameter this collar.

In the alternative embodiment of the present invention shown in FIG. 4 the radiopaque markers formed by marker 57 and spring coil 48 are arranged in what is known as a "book end" position. That is, the marker 57 is placed at the proximal end of the balloon 18 and the marker 48 is adjacent to the distal end of this balloon. In this configuration the implanting physician positions guide wire 22 such that spring coil 48 is distal to the target lesion and radiopaque marker 57 is proximal to the target lesion. In this manner, balloon 18 is positioned across the lesion. Additionally, in accordance with the teachings of the present invention catheter 10 itself can be provided with an additional radiopaque marker such as radiopaque ring 74, which is preferably a metallic band, such as platinum, for example, affixed to distal end 58 of tubular body 38. Radiopaque ring 74 enables the vascular physician to confirm that balloon 18 is properly positioned relative to collar 46 by lining up radiopaque ring 74 with radiopaque marker 57. This may be particularly helpful during reengagement of sleeve 42 with cylindrical collar 46.

In an alternative embodiment illustrated in FIG. 4A, the radiopaque ring marker 74 is encapsulated between the distal end 58 of the tubular body 38 and the proximal end 62 of the balloon 18. The proximal end of the balloon 18 is heat shrunk to the tubular body 38, simultaneously creating a seal between the balloon 18 and the body 38, and encapsulating the ring marker 74. The encapsulation process is performed with a mandrel placed through the axial lumen 20 to provide a smooth inner surface for the lumen 20 and to ensure that the diameter of the lumen 20 remains constant around the encapsulation zone. It will be appreciated that the ring 74 can also be encapsulated by using adhesive or another polymer or an encapsulant such as polyethylene. This encapsulation preferably extends throughout the ring 74 to create a tight seal between the balloon 18 and the tubular body 38. Such encapsulation allows the ring 74 to be effectively secured in place, and promotes smoother guide wire movement through the axial lumen 20. Such encapsulation also allows for a larger diameter for lumen 20 and faster balloon deflations due to the improved fluid flow. It will be appreciated that essentially the same type of marker encapsulation of a ring 74 can also be achieved with the embodiment of FIG. 2A where the tubular body 38 extends across the balloon 18 and through the resilient sleeve 42.

To facilitate the functioning of the releasable sealing means (valving device 41) of the present invention, it is preferred that collar 46 have a generally uniform circular cross section to define a smooth cylindrical outer surface. However, as shown in FIG. 5, it is contemplated as being within the scope of the present invention to provide collar 46 with a slightly tapering proximal end 78 to ease the initial engagement of resilient sleeve 42 over collar 46 as balloon 18 is advanced along guide wire 22. Additionally, to provide a more secured sealing engagement collar 46 can be configured to include a circumferential groove 80. Alternatively, the proximal end of collar 46 adjacent to retaining beads 54 and 56 may be provided with a hemispherical cross section for the same purposes as is shown in the alternative embodiment of FIG. 4. Similarly, beads 54 and 56 can be configured for this purpose.

Another advantage of the present invention is that the guide wire 22 may be sealingly disengaged, sealingly reengaged, removed, or replaced by another guide wire, for example, the guide wire assembly may be replaced with a guide wire assembly having a different stiffness. In other words, the physician may want to use a guide wire which is more flexible, or a guide wire which is stiffer and more pushable. Because the lumen 20 has a size everywhere along its length which is large enough to pass the enlarged-diameter distal end valving portion 26 of the guide wire 22, this replacement of the guide wire assembly 22 is easily accomplished. Referring to FIG. 5A, the collar 46 may also be provided with a tapered distal end 82. This tapered distal end of the collar 46 facilitates easier guide wire replacement It also should be emphasized that axial lumen 20 of the present inventive catheter assembly 10 is configured to perform a dual role. As shown in FIG. 2, the diameter of axial lumen 20 is greater than that of guide wire 22, including the distal collar portion 46. By virtue of this construction, axial lumen 20 is adapted to both receive guide wire 22 and to conduct an inflation fluid to and from balloon 18. This dual function design produces an ultra-low profile balloon catheter device which significantly enhances the ability of the catheter to cross very tight stenoses or to traverse particularly difficult vascular pathways. As an additional benefit, larger volumes of radiographic visualization dyes may be injected around the tubular body 38 and through the positioning or guide catheter (not shown) to enhance visibility of the arterial lumens during placement of the apparatus. This increased volume of radiographic dye and improved visibility is common with small-diameter catheter assemblies in comparison to the larger-diameter conventional balloon catheters.

Along these lines, exemplary non-limiting dimensions for the balloon catheter assemblies of the present invention may be as follows. For example, as is typical in the coronary arts, the overall length of catheter 14 will typically range from 120 cm to 160 cm. The axial length of dilatation balloon 18 will comprise approximately 1 cm to 4 cm of this overall length, while an embolectomy balloon will be about 0.5 cm to 2.0 cm of this overall length. Typically, dilatation balloons are available in stepped diameters ranging from approximately 1.0 mm to 5.0 mm in 0.5 mm or 0.25 mm increments, while the stepped inflation diameters of embolectomy balloons range from approximately 1 mm to 9 mm in 0.5 mm or 0.25 mm increments. As known in the art, these inflation diameters are typically characterized at 6 to 10 atmospheres of pressure for dilation. Naturally, the deflated profile of the dilatation balloons increases slightly with increases of the final dilation diameters. However, while the majority of prior art balloon catheters have a deflated balloon profile measuring approximately 0.04 inches in diameter, the balloon catheter of the present invention has a typical dilated balloon profile of only 0.03 inches. Similarly, the dual function, single lumen design of the present invention produces a tubular shaft having a correspondingly narrow profile.

Exemplary non-limiting diameters for the proximal portion of guide wire 22 range from 0.005 to 0.016 inches whereas the preferred exemplary outer diameter of cylindrical collar 46 ranges from approximately 0.012 to 0.018 inches. Thus, in the embodiments of the present invention illustrated in FIGS. 1–5A, the distal end portion of guide wire 22 is provided with a cross-sectional diameter on the order of approximately 0.005 inches and cylindrical collar 46 is formed of a polymeric material such as PTFE having an outer diameter of approximately 0.016 inches and a wall thickness of approximately 0.005 inches. It should be emphasized that the proximal diameter of guide wire 22 need not be constant and may taper to provide an enhanced degree of flexibility toward the distal end of guide wire 22. Guide wire 22 itself is preferably formed of metal such as stainless steel but also may be constructed of polymers or of polymer-coated metals, as is known in the art. An exemplary overall wire length for guide wire 22 is on the order of 175 cm. The cross section of guide wire 22 proximal to cylindrical collar 46 need not be circular to be within the scope of the present invention. For example, generally elliptical or ribbonlike configurations may be utilized to provide an enhanced degree of flexibility.

Also visible in FIGS. 2A and 2B, is a balloon-centered radiopaque marker 76 formed as a band of dense metal, such as gold or platinum, for example, fixed at a centered position proximal to the distal end portion of wire 22. Marker 76 can be secured to tubular body 38 in any manner known in the art including encapsulation, adhesives, or simple mechanical deformation, and is analogous to the marker 57 pointed out above. Radiopaque marker 76 functions to provide the implanting physician with a readily apparent visual reference which be viewed on a fluoroscope during the angioplasty procedure. During positioning of the apparatus the surgeon simply manipulates the catheter assembly of the present invention until marker 76 is positioned directly adjacent or centered in the target lesion. Because of its positioning on tubular body 38 relative to dilatation balloon 18, when marker 76 is so positioned, dilatation balloon 18 is positioned across the lesion as well.

Further details of the balloon exchange or replacement procedure in accordance with the teachings of the present invention will be discussed with respect to FIGS. 6–16. As noted above, the exchangeable integrated-wire balloon catheter of the present invention enables a vascular physician to exchange one catheter for a second catheter along the pre-positioned guide wire without having to retrace the entire vascular pathway with the guide wire. As those skilled in the art will appreciate, replacement balloons produced in accordance with the teachings of the present invention need not include a guide wire. Thus, as is illustrated in FIG. 6, an exemplary replacement catheter assembly 10 can be provided with its balloon 18 pre-folded over a disposable mandrel 84 and packaged in disposable balloon cover 86. Preferably, mandrel 84 is constructed of metal or plastic and approximates the outer diameter of collar 46. Additionally, mandrel 84 may be coated with lubricating materials such as PTFE or silicone.

The cross section of FIG. 7 illustrates an exemplary folded profile of balloon 18 for use in packaging within balloon cover 86. Viewing FIG. 6, the mandrel 84 is preferably tapered such that the diameter of the mandrel at point 88 is wider than the diameter at point 90. This tapering facilitates easier removal of the mandrel 84 and also facilitates reengagement of the collar 46 to allow collars 46 of different sizes on different guide wires to be fitted sealingly into the sleeve 42 of the catheter assembly 10.

Turning next to FIG. 8, in order to position the replacement catheter over a guide wire, the mandrel 84 is first removed, the catheter is flushed, and then the balloon cover 86 is removed. This allows the folded balloon 18 illustrated in FIG. 8 to freely pass over the smaller diameter proximal portion of guide wire 22 (not shown) as the implanting physician advances the replacement catheter along the guide wire. This folded balloon arrangement also supplies additional columnar strength to the replacement catheter which enables the implanting physician to easily engage resilient sleeve 42 over collar 46 to seal and inflate balloon 18, as was previously illustrated in FIGS. 3 and 4, for example.

Returning for a moment to a consideration of FIG. 1, an additional feature of the present invention is the provision of exit markers 92 and 94 distally of the Y-connector 12 on the tubular body 38 as shown in FIG. 1. Generally speaking, exit markers 92 and 94 inform the implanting physician that catheter assembly 10 is advancing within a tubular guide catheter (not shown) to a position near its intended target at which the tip of the balloon 18 is about to exit a distal end of this guide catheter. At this point the implanting physician can activate a fluoroscope to assist in the visualization and final placement of the balloon 18 across the target lesion. Preferably, as illustrated in FIG. 1, two exit markers are utilized. The first, marker 92 will preferably be positioned approximately 90 cm from the distal end of balloon 18 and can be utilized to indicate tip exit from a guide catheter positioned for a brachial approach. Similarly, marker 94 is preferably positioned approximately 100 cm from the distal tip of the catheter to indicate exit from the guide catheter during a femoral approach. Both markers 92 and 94 may be applied to catheter 30 through printing, stenciling, embossing or the like.

Along these lines, as illustrated in FIG. 9, it is also contemplated as being within the scope of the present invention to provide the proximal end of guide wire 22 with its own set of visual markers, 96 and 98, to assist the implanting physician in determining that sleeve 42 is engaged with cylindrical collar 46. For example, it is contemplated that marker 98 would be positioned approximately 170 cm from tip 50 of wire 22 and would signal that a replacement catheter tracking over the wire is about to exit the guiding catheter. It should be noted that this positioning is appropriate for both the femoral and brachial approaches. However, marker 96 is preferably positioned approximately 142 cm from tip 50 of wire 22 and functions to assure the implanting physician that resilient sleeve 42 is engaged with cylindrical collar 46. In practice, the implanting physician would visually align marks 96 and 98 with the outer visual reference formed by the proximal end of torquer 32 on Y-connector 12 illustrated in FIG. 1.

Figure 11:
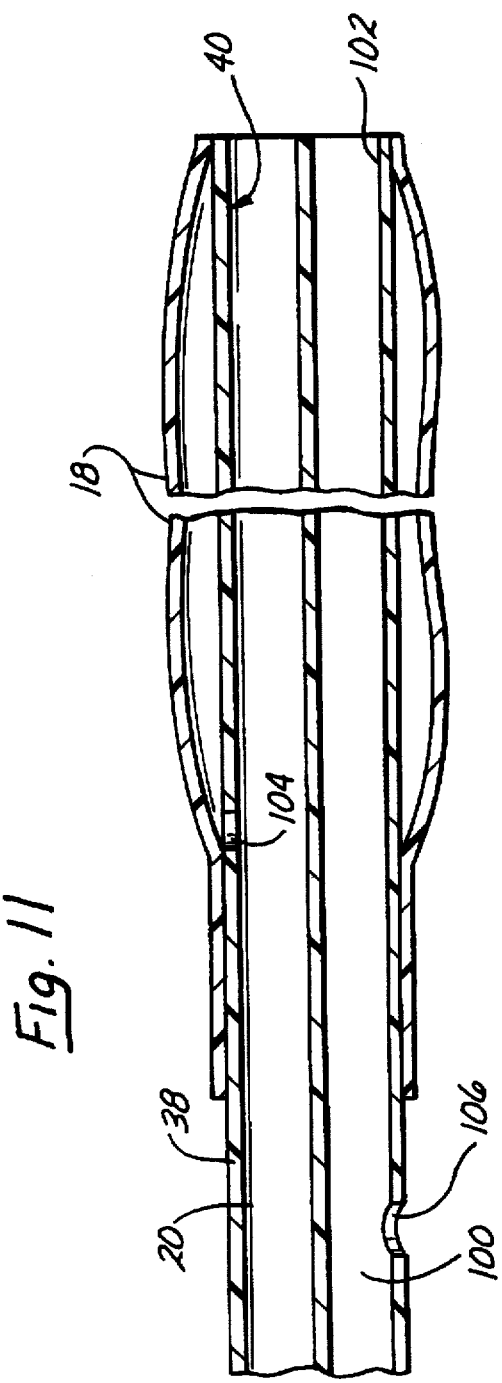
FIG. 11 is an enlarged cross-sectional view of the distal portion of an alternative dual-lumen balloon catheter illustrating additional features of the present invention.

Alternative exemplary embodiments of the exchangeable integrated-wire balloon catheter of the present invention are illustrated in FIGS. 10 and 11. In order to obtain reference numerals for use in describing the structure of FIGS. 10 and 11, the prior practice of referring to features which are the same as, or analogous in structure or function to, a feature depicted and described above is continued. Each of these alternative embodiments is provided with an additional fluid conducting lumen. More particularly, the alternative embodiment of FIG. 10 illustrates a catheter embodiment configured for distal infusion of drugs, blood or other fluids. In addition to lumen 20, this alternative embodiment includes a second lumen 100 which serves to conduct fluids from the proximal end of the tubular shaft 38 of catheter assembly 10 to its outlet port 102 adjacent to the resilient sleeve 42 on balloon 18. It should be noted that either or both lumens may be sized to sealingly engage the enlarged distal end portion of the guide wire 22. In this alternative embodiment, a side opening or communication port 104 is provided in lumen 20 to enable lumen 20 to communicate with balloon 18 for purposes of inflation and deflation. The alternative double-lumen embodiment of the present invention illustrated in FIG. 11 is structured to allow the passage of blood from proximal of the balloon 18 to the distal end of the balloon while this balloon is inflated. Thus, in addition to dual-function axial lumen 20 catheter assembly 10 of FIG. 11 also is provided with a second lumen 100 which, in turn, is provided with at least one distal outlet port 102 and at least one proximal side opening or perfusion inlet port 106. Inlet port 106 allows blood to passively perfuse the artery distally of the balloon 18 during inflation of the balloon. This perfusion blood flow is provided the passageway for blood to enter additional lumen 100 through port 106 and exit through distal port 102.

Figure 12:
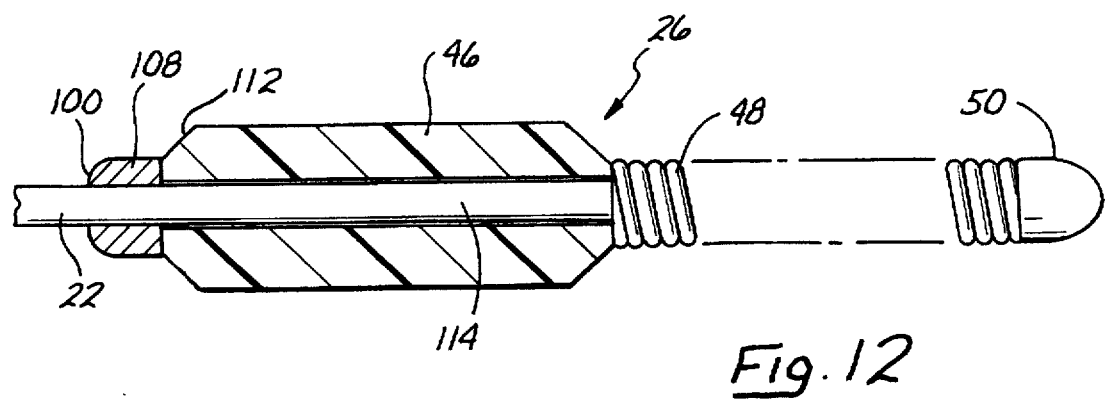
FIG. 12 provides a fragmentary cross sectional view of yet another alternative embodiment for a distal end portion of a guide wire for use with the catheter assembly of the present invention.

Referring now to FIG. 12, yet another alternative embodiment of the present inventive catheter assembly is depicted. FIG. 12 shows the distal end portion 26 of a guide wire 22 in which an additional bandlike radiopaque marker 108 is provided proximally of and adjacent to the collar member 46. The marker 108 may be formed of any appropriate material, and is secured on the guide wire 22 so that it captures the collar member 46 in cooperation with the coil 48. Preferably the marker 108 includes a proximally disposed chamfer or taper surface 110 which is of assistance when a catheter is to engage the collar 46 at sleeve 42. That is, the tapered surface 110 of the marker leading to a chamfered proximal surface 112 on the collar member 46 virtually eliminates any possibility that the distal end 16 of the catheter will catch on the marker or collar as the catheter advances distally along the guide wire assembly 22.

FIG. 12 also shows that the collar member 46 may be molded in place on the guide wire 22. To achieve this molded-in-place collar member, the guide wire 22 may be placed in a mold, for example, and the polymeric material of collar 46 in a semi-liquid molten condition is then is forced or injected into the mold around the wire 22. For this purpose, a surface portion 114 of wire 22 would be coated with a release compound, and also may be highly polished to inhibit sticking of the injected polymeric material on the surface portion 114. With the proper release compound, and possibly with the selection of a highly polished surface finish on surface portion 114, and also possibly in conjunction with the control of the temperature and pressure at which polymeric material is injected to form the collar 46, the radial clearance of the collar member 46 at surface 114 can be so small as to virtually eliminate leakage of pressurized inflation fluid axially along this interface. This virtual elimination of axial leakage is important because the volume of the dilatation an embolectomy balloons is rather small, and the delivery of pressurized fluid along the long and rather narrow catheter shaft results in some considerable pressure loss during fluid flow conditions. Consequently, a leak of pressurized fluid at the collar 46 can result in the balloons not being inflated as forcefully or a firmly as is desired. On the other hand, by virtually eliminating axial leakage at the interface between the wire 22 and the collar member 46, the embodiment of the present invention presented by FIG. 12 helps assure a complete and forceful inflation of the balloon 18.

Figure 13:
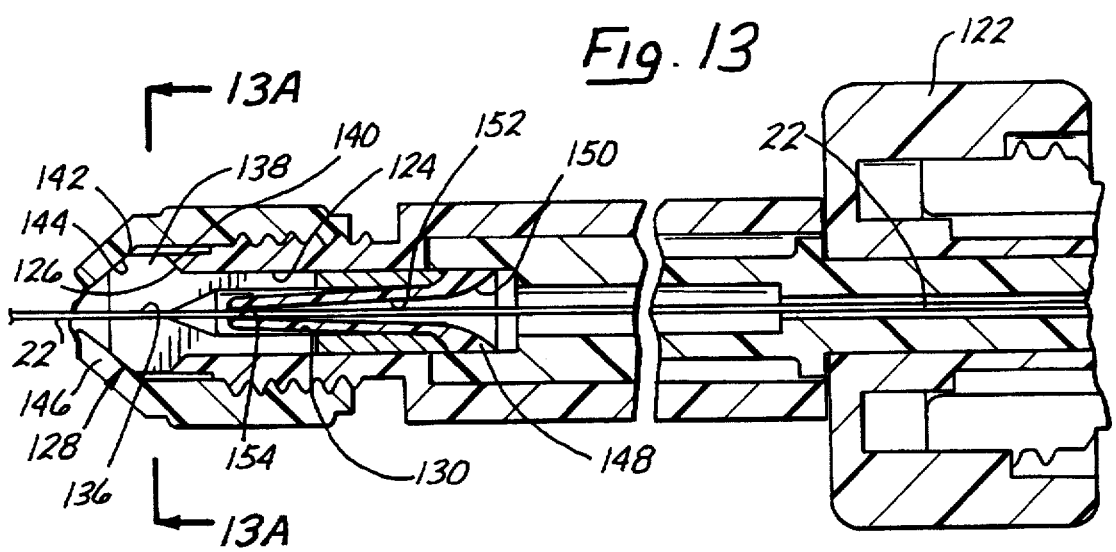
FIG. 13 presents a fragmentary cross sectional view of a torquer portion of a proximal Y-connector of the catheter assembly seen in FIG. 1.

Viewing FIG. 13, a fragmentary cross sectional view of the torquer 32 is presented. This torquer is rotationally carried at the proximal end of the Y-connector 12, and provides for the physician to selectively engage the guide wire 22 in order to twist or rotate this guide wire along its length within the catheter assembly 10. As those ordinarily skilled in the pertinent arts will appreciate, the distal end portion 26 of the guide wire projects forwardly of the catheter shaft along a vascular pathway which the physician desires to negotiate with the catheter 10, and may be pre-curved or otherwise formed in order to assist in achieving entry into a coronary artery, for example.

Figure 13A:
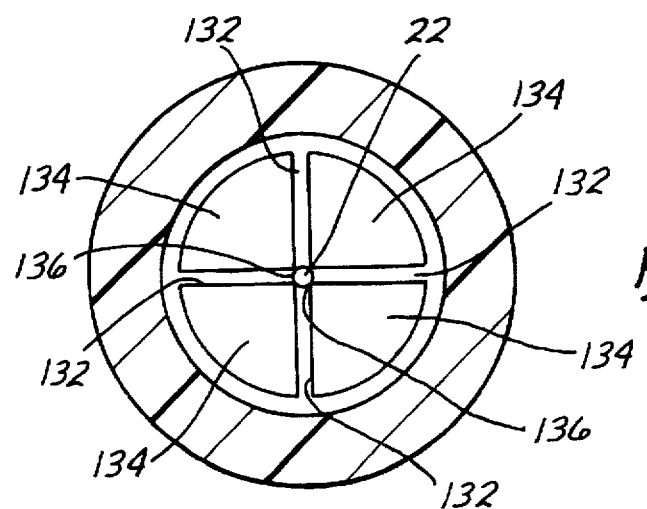

Considering FIG. 13, it is seen that the torquer 32 includes a body portion 116 which defines an axially extending stepped through bore 118, through which the proximal portion 24 of the guide wire assembly 22 extends. At its distal end, the body 116 includes an axially projecting boss portion 120 which is captured rotationally in a ring member 122. The ring member 122 threadably engages the proximal end of the Y-connector 12. At its opposite, or proximal end, the bore 118 includes a larger diameter bore portion 124 leading to a tapering portion 126. Received in the bore portion 124 is a collet member 128, a part of which is also seen in FIG. 13a. This collet member 128 is preferably formed of metal, and brass is the preferred metal for this use because it will not damage the guide wire 22. This collet member 128 includes a through bore 130, through which the guide wire 22 passes, and a pair of transverse slots 132 which intersect at the center of the bore 130 to proximally separate the collet member into four separate jaw members 134, each having a pointed edge 136.

Externally, the collet member 128 includes an enlarged portion 138 which distally defines a tapered surface 140 engaging the tapered surface 126 of the body 116. Proximally, the enlarged portion 138 defines a similar tapered surface 142 which is engaged by a tapered surface 144 of a ring member 146. The ring member 146 itself threadably engages the body 116. Consequently, tightening of the ring member 146 forces the tapered surfaces 142 and 144 together, and forces the collet member 128 into the bore 124 to force surface 140 into engagement with the tapered bore portion 126. The result is that the jaws 134 at their pointed edge 136 engage the guide wire 22, as can be appreciated by viewing FIG. 13a, to allow the physician to twist this wire by rotating the torquer 32 relative to the Y-connector 12. However, as can be appreciated by viewing FIG. 13a, the guide wire 22 is of small size. For example, the guide wire 22 may be only of 0.014 inches diameter. Yet, this small wire must be gripped along the pointed edges 136.

In order to insure that the guide wire is centered along these edges 136, the torquer 32 includes a polymeric internally tapering guide member 148. This guide member 148 is received into the bore 130 of the collet member, and defines a funnellike entrance portion 150 leading to a tapering guide portion 152, and to a cylindrical guide portion 154 immediately distal to the edges 136 of the jaws 134. Consequently, the guide wire 22 is centered in the collet member 128 and is retained along the edges 136 for driving engagement by these edges when the torquer 32 is tightened. Also, the guide member 148 serves an additional purpose when the catheter is advanced over a placed guide wire 22 and along this wire to a treatment site. In this case, the proximal end of the guide wire 22 is introduced into the distal end of the catheter assembly, and these two assemblies are relatively moved so that at the torquer 32, the proximal end of the guide wire enters first the funnellike portion 150, the guide portion 152, the guide portion 154, and then the jaws 134. Consequently, the proximal end of the guide wire 22 is guided progressively toward its position of centering in the jaws 134, slides proximally of these jaws, and the guide wire 22 does not hang up on the torquer 32.

Figure 14:
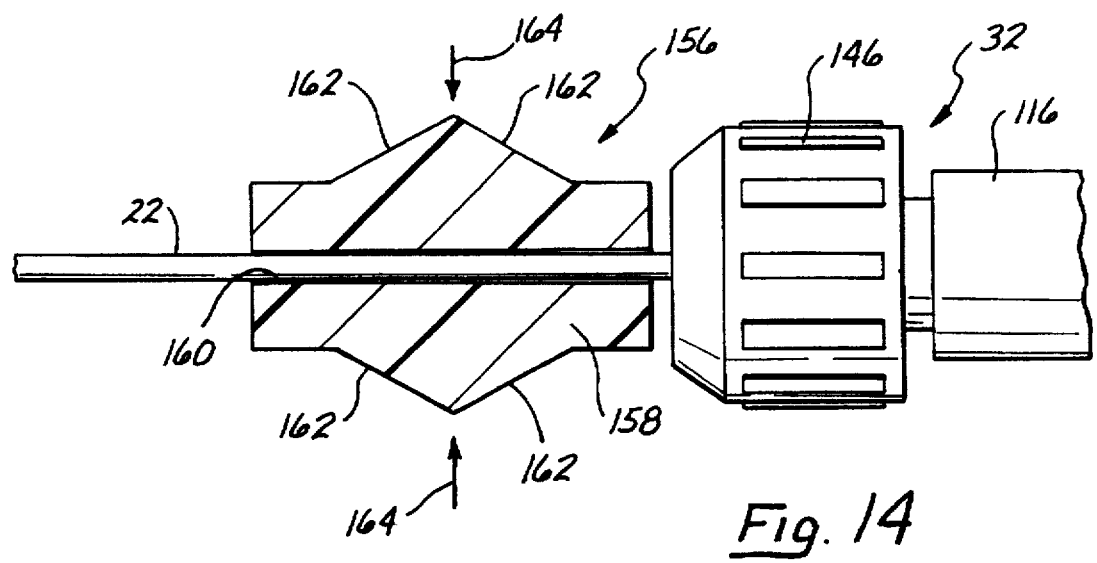
FIG. 14 is a fragmentary side elevation view of an alternative embodiment of the catheter assembly according to the present invention.

FIG. 14 shows an alternative embodiment of the present invention in which a disengagement device 156 is provided on the guide wire 22 proximally of the torquer 32 in order to provide for the physician an improved grip on this guide wire when the physician desires to disengage the collar 46 from the sleeve 42 by relative axial movement of the catheter assembly 10 and wire 22. For this purpose, the disengagement device 156 is formed as a tubular body 158 of elastic material which will afford a high coefficient of friction on the wire 22. The body 158 defines a bore 160 which is sized to slidably pass the guide wire 22. Externally, the body 158 defines grip surfaces 162 at which a physician may manually apply gripping pressure, as is indicated by the arrows 164. Under these conditions, the body 158 is compressed such that the bore 160 of the body 158 is deformed to grip the wire 22, and provides a better grasp on this wire than the physician could achieve with just the gloved fingers. Consequently, the wire 22 is more easily and certainly moved axially relative to the catheter assembly 10 in order to effect the disengagement or engagement of the collar 46 from or into the sleeve 42.

Figure 15:
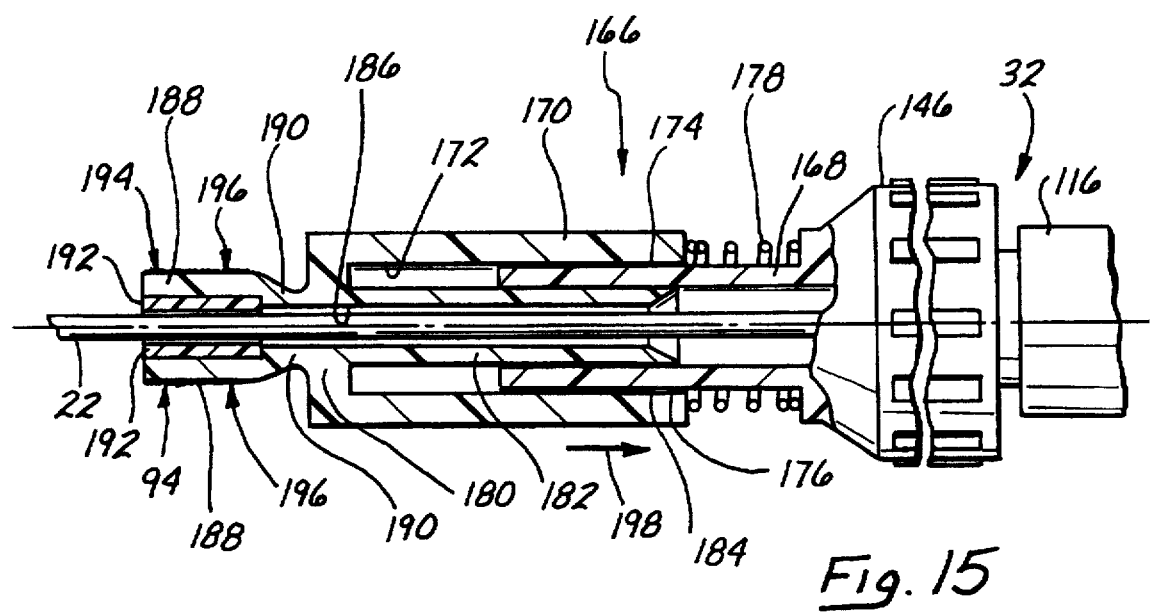
FIG. 15 presents a fragmentary cross sectional view of yet another alternative embodiment of the present catheter assembly in which a proximal Y-connector also includes a disengagement device for gripping and axially relatively moving the guide wire of the catheter assembly.
Figure 16:
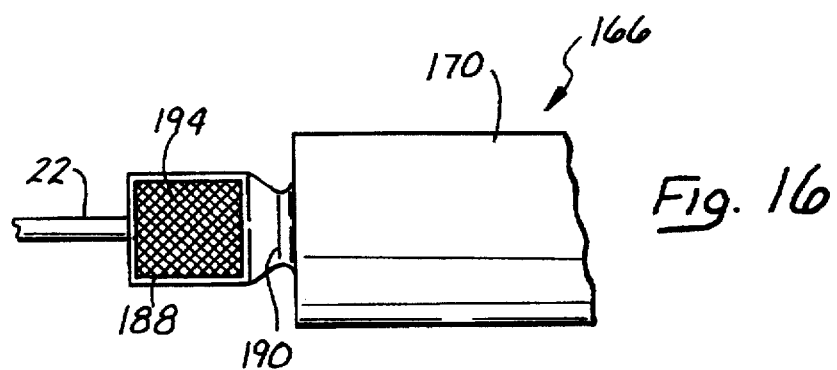
FIG. 16 provides a fragmentary plan view of the disengagement device portion of the catheter assembly fragmentarily seen in FIG. 15.

FIGS. 15 and 16 provide respective fragmentary cross sectional and plan views of yet another alternative embodiment of the present invention. This embodiment includes a torquer 32 which carries proximally a disengagement device, generally referenced with the numeral 166. This disengagement device 166 has the same purpose as the disengagement device 156 seen in FIG. 14. However, the device 166 includes a proximally extending tubular boss portion 168 which is carried by the ring 146 of the torquer 32. Slidably carried on the tubular boss 168 is a tubular member 170 defining a stepped through bore 172. The tubular boss member 168 outwardly defines a circumferential ridge 174, and the body 170 at the distal end of bore 172 inwardly defines a lip 176. The body 170 can be forced onto the boss 168 distally of the ridge 174 by forcing lip 176 over this ridge. Once the body 170 is so disposed on the boss 168, these two features are slidable axially relative to one another, but the body 170 is captively retained on the boss 168. A coil compression spring 178 is carried on the boss 168 between the ring 146 and the body 170 to yieldably urge the latter toward a first proximal position thereof.

Still viewing FIG. 15, the body 170 includes an end wall 180 through which the stepped bore passes with a diameter just sufficient to pass the guide wire 22. Distally from the wall 180, body 170 also includes a tubular guide portion 182 extending distally into the inside of the boss 168. At its distal end, this tubular guide portion 182 defines a funnellike entrance surface 184. Inwardly, the guide portion 182 defines a proximally tapering portion 186 of the bore 172. Proximally of the wall 180, the body 170 includes a pair of opposed gripper members 188. These gripper members 188 are preferably integral with the remainder of body 170, and are attached thereto by flexible integral hinge sections 190. Inwardly, each of the gripper members 188 carries an elastic gripper pad 192, each of which confronts the guide wire 22. Outwardly, the gripper members 188 define a textures surface 194 for manual engagement of the gripper pads 192 with the guide wire 22, as is depicted by the arrows 196.

In use of a catheter assembly including a disengagement device as depicted in FIGS. 14 and 15, the physician manually squeezes the gripper members 188 onto the guide wire 22, and advances the body 170 distally to a second position (as is indicated by arrow 198) to disengage the collar 46 from within sleeve 42. The spring 178 insures that the body 170 is maintained in the first or proximally-located position preparatory to this distal disengaging movement by the physician. Thus, the physician need not back off the body 170 with respect to the torquer 32 preparatory to disengaging the collar 46 from sleeve 42. Additionally, the available distal movement of the body 170 is designed to insure disengagement of the collar 46 from within sleeve 42 with only a single distal movement of the body 170. Consequently, the physician simply grips the members 188 and strokes the body 170 distally one time relative to the Y-connector 12 to insure disengagement of the collar 46 from within sleeve 42, and opening of the distal port 40.

FIGS. 17-34 present alternative embodiments of the present inventive catheter having various alternative constructions for the valving device 41 are shown. In order to obtain reference numerals for use in describing all of these alternative embodiments to the valving device 41, features which are the same as or are analogous in structure or function to features depicted and described above are referenced with the same numeral. In cases where a feature is analogous in structure or function to a prior feature, but an additional aspect of that feature exists which the reader should notice, this feature is referenced with a familiar numeral having a prime added thereto, and additional explanation is provided of the noteworthy variation.

Viewing FIG. 17, it is seen that the collar member 46' is tapered so that this collar member decreases in diameter in the proximal direction. The collar member 46' is fabricated of Teflon like the collar 46 seen in FIGS. 1-5A, and FIG. 9, and is consequently very stable dimensionally. Bonded within the sleeve 42 of balloon 18 at the orifice 40 is a dimensionally stable valving tube member 200. The tube member 200 may be fabricated of metal, but preferably is fabricated of polyimide material. The valving tube 200 is secured within sleeve 42 by a layer 202 of adhesive. The embodiment of the valving device 41 seen in FIG. 17 has an advantage in that the material of balloon 18 is generally shrink tubing, or is shrunk or thermally processes from another size to the size of the sleeve structure 42 seen in FIG. 2, for example. A consequence of this thermal processing is that the polymer material may retain a memory of its former size and configuration.

Over time, especially with thermal cycling, the polymer material of the sleeve 42 may creep slightly back toward its former size and configuration. Because the valving device 41 as seen in FIG. 2 relies for its sealing integrity on the closeness of fit between the collar 46 and the inside surface of sleeve 42, after a period of time the sealing integrity at the valving device 41 may not be as good as at the time when the catheter 10 was manufactured. In other words, the catheter 10 may deteriorate somewhat in a functional sense with the passage of time and regardless of what high level of quality control is exercised in its initial manufacture. On the other hand, the embodiment of the present invention seen in FIG. 17 may enjoy an improved shelf life because of the dimensional stability of the tube member 200 without any significant loss of sealing integrity at the sealing device 41.

Figure 18:
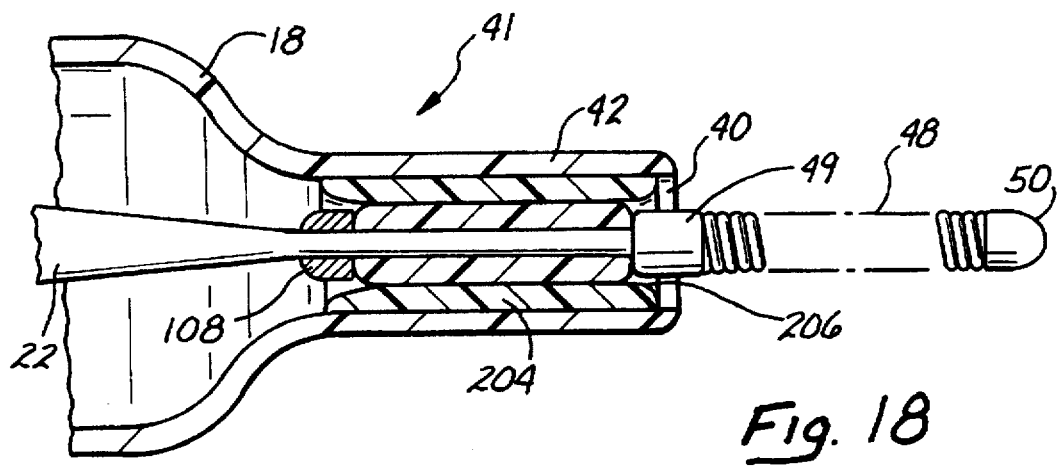

Another alternative embodiment of the present inventive catheter assembly 10 and guide wire assembly 22 is seen in FIG. 18. This alternative embodiment also offers the advantage of decreased reliance on dimensional precision at the collar 46 and sleeve 42, as was seen in the embodiment of FIG. 17. Viewing FIG. 18, the guide wire assembly 22 is seen to be the same as that seen in FIG. 17. However, at the sleeve 42, a comparatively thick internal annular layer 204 of resilient elastic or resilient material is provided. The material layer 204 may be made of silicone, for example, or of a material such as linear low-density polyethylene. Significantly, the material layer 204 is sufficiently thick that it is sealingly conformal to the external surface of the collar member 46, as is seen in FIG. 18. That is, the elastic or resilient layer 204 may contract slightly distally of the collar 46 to form a radially inwardly extending shoulder 206. The shoulder 206 of elastic or resilient material layer 204 in conjunction with the distal taper of the collar member 46 will serve to form a detent feature for the collar member 46 in the sleeve 42.

The embodiment of the present inventive catheter seen in FIG. 18 has the significant advantage of providing a reliable seal at the valving device 41 even if the material of sleeve 42 should creep slightly with aging of the catheter assembly 10. That is, the material layer 204 is sufficiently conformal that a seal is formed with the collar 46 even if the sleeve 42 supporting the material 204 has distorted or crept slightly with the passage of time since the catheter 10 was manufactured. In this way, the embodiment of FIG. 18 also has a comparatively high tolerance to dimensional imprecision at the valving device 41.

Figure 19:
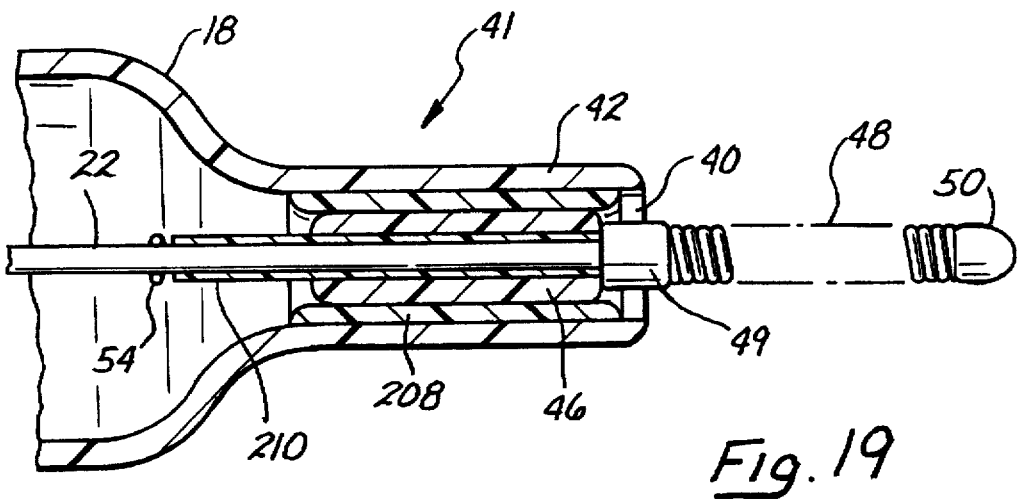

Yet another alternative embodiment of the present invention which also offers a high tolerance to dimensional imprecision is seen in FIG. 19. Viewing FIG. 19, it is seen that the collar 46 is cylindrical and round-like that seen in FIGS. 1-5A, for example. This collar 46 is sealingly received into a resilient and yieldably shape-retaining annular layer 208 of thermoplastic material. The thermoplastic material of layer 208 helps to retain dimensional stability at the sleeve 42, and is heat sized at manufacture of the catheter assembly 10 to precisely fit in sealing relation with the collar member 46. Also, in contrast to the embodiments seen earlier, the collar member 46 of FIG. 19 is carried sealingly on a thin-walled tube member 210 which is rotationally carried on the guide wire assembly 22. The tube member 210 forms a very small running clearance with the guide wire 22 so that this tube member is relatively rotatable, but also forms a long, or capillarylike, relationship with this guide wire so that fluid leakage between the tube member 210 and wire 22 when the balloon 18 is pressurized is significantly reduced. Preferably, the tube member 210 may be fabricated from polyimide material.

FIG. 20 depicts yet another alternative embodiment of the present invention which employs a guide wire assembly 22 like that seen in FIG. 19. That is, the guide wire assembly 22 includes a tube member 210 which rotationally carries the collar member 46 upon the guide wire. However, at the sleeve 42, a tubular thermoplastic member 212 is bonded at 214 and extends distally to define a sleeve section 42' which is axially separated from the sleeve 42 of the balloon 18. The sleeve section 42' sealingly engages with the collar 46 of the guide wire assembly 22. That is, the sleeve 42' is isolated from dimensional creep of the sleeve 42 by its axial separation from this sleeve 42.

Figure 21:
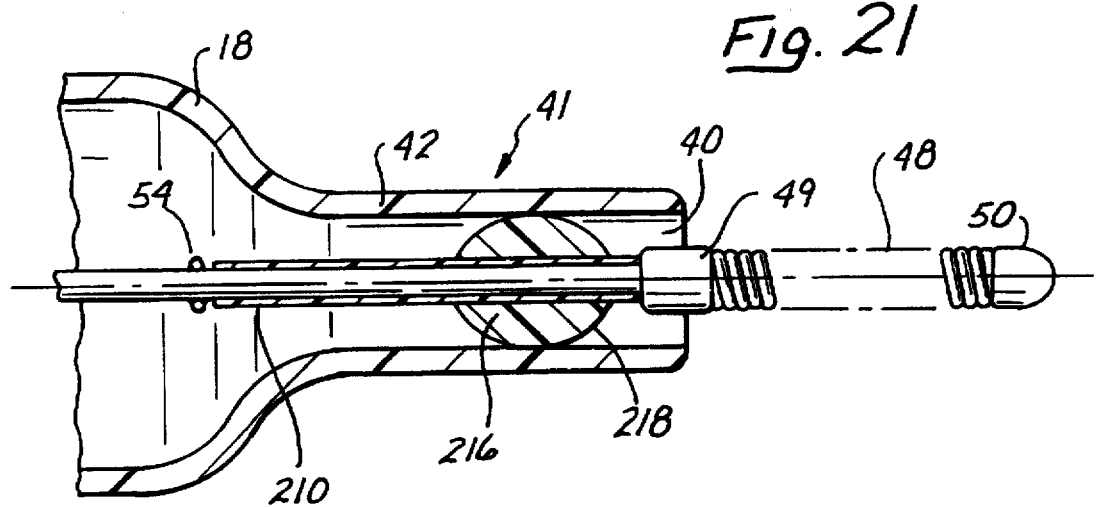

FIG. 21 provides a fragmentary cross sectional view of yet another alternative embodiment of the present invention. This embodiment also offers a particularly advantageous freedom with respect to dimensional tolerance at the valving device 41. The embodiment of the invention seen in FIG. 21 includes a tube member 210 like that seen in FIGS. 19 and 20. However, the tube member 210 of FIG. 21 carries an ellipsoid-shaped body 216 of shape-conformal elastic or resilient material. The body 216 may be formed on the tube member 210 by injection or transfer molding of silicone, for example. Alternatively, the body 216 may be formed from a length of silicone tubing which is adhesively bonded onto the tube member 210. The surface 218 of body 216 is preferably treated both to improve its abrasion resistance and to lower its coefficient of friction. An ion discharge treatment, for example, which is conventional, may be used to achieve these variations in the surface molecular properties of silicone material.

The ellipsoid body 216 is a body of rotation and is disposed on the tubular member 210 with its major axis parallel with the orifice 40. Of course, when viewed in a direction parallel with the axis of orifice 40, the body 216 is circular in shape. Consequently, when drawn into the sleeve 42, the body 216 is distorted from its ellipsoid shape to sealingly cooperate in closing the orifice 40. This sealing cooperation of the body 216 in the sleeve 42 is effective despite dimensional variations and out of round distortions, for example, which may have occurred in or since manufacture of the sleeve portion 42. Consequently, the embodiment of FIG. 21 also offers a great freedom with respect to dimensional tolerances at the valving device 41 while still achieving a very good control of fluid leakage at the orifice 40.

Figure 22:
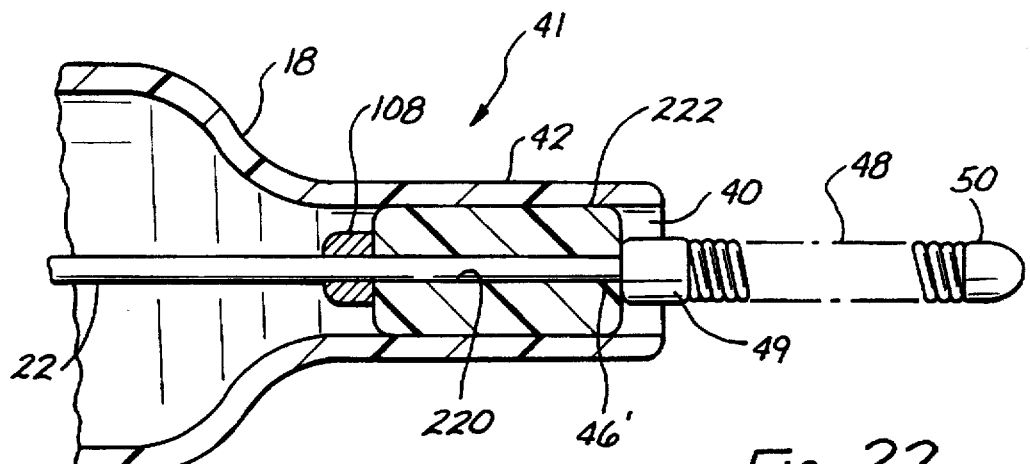

Still another alternative embodiment of the present invention is seen in FIG. 22. At first blush, this embodiment of the invention appears to be the same as that of FIG. 12, for example. However, the embodiment shown in FIG. 22 includes a valving device 41 having a resilient collar member 46' captured between the braze 49 and the marker 108. That is, the Collar member 46 is yieldably shape-conformal in nature. The collar member 46' is preferably fabricated of silicone or other elastic or resilient material to be received in radial compression between the sleeve 42 of the balloon 18, and the surface of the guide wire assembly 22. That is, in its free or undistorted condition, the collar member 46' defines an inner diameter slightly smaller than the local diameter of guide wire assembly 22, and an outer diameter slightly larger than the inner diameter of sleeve 42. When the collar member 46' is received on the guide wire assembly 22, its outer diameter may be increased slightly because the collar member is stretched to receive the guide wire 22.

Subsequently, when the collar member 46' is received into the sleeve 42, the collar member is radially compressed to sealingly cooperate with the sleeve 42. Also preferably, the inner and outer surfaces 220 and 222, respectively, of the collar member 46' are treated as outlined above to improve their abrasion resistance and lower their coefficient of friction. Consequently, the collar member 46' is slidably receivable into the sleeve portion 42 to sealingly cooperate therewith, and is rotational on the guide wire assembly 22 to also sealingly cooperate with this guide wire. The result is that the yieldably shape-conformal and elastic or resilient collar member 46' provides a considerable tolerance to dimensional variations at the sleeve 42 and guide wire 22 while still providing excellent sealing cooperation with these structural elements and allowing relative rotation therebetween.

Figure 23:
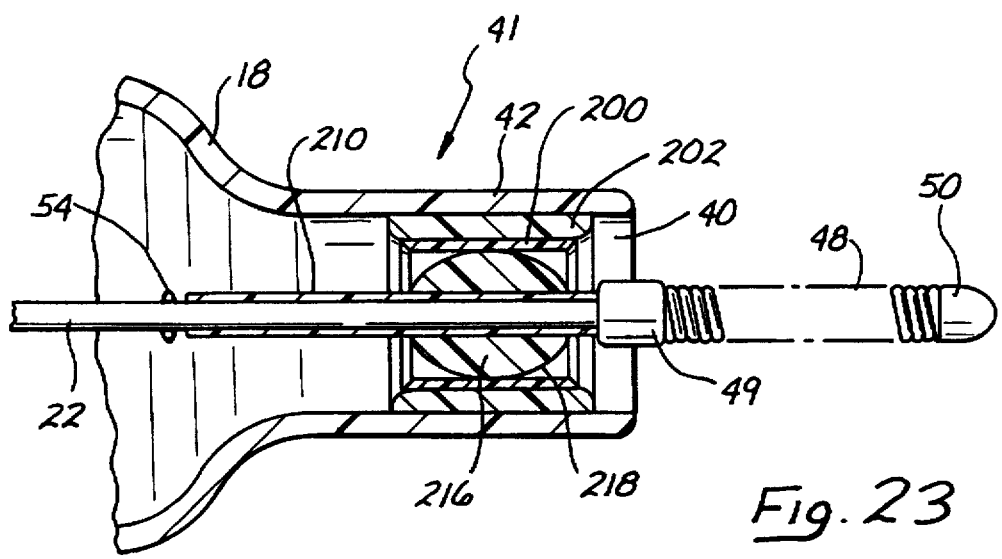

Turning now to FIG. 23, yet another alternative embodiment of the present invention is depicted. FIG. 23 shows a guide wire assembly 22, like that described above with reference to FIG. 21, used in combination with a catheter assembly like described above with reference to FIG. 17. In other words, an elastic or resilient body 216 carried on a tube member 210 upon the guide wire assembly 22 is sealingly received into a dimensionally stable tube member 200 secured into the sleeve 42 by a layer of adhesive 202. This embodiment of the invention offers the dimensional stability at the orifice 40 achieved by the added stability of the tube member 200, and the compliant sealing nature of the elastic or resilient body 216 carried rotationally with the tube 210 on the wire assembly 22. Again, a very low level of leakage is achieved at the valve device 41 shown in FIG. 23, while a good tolerance to dimensional variations at this device is achieved with reliable sealing.

Figure 24:
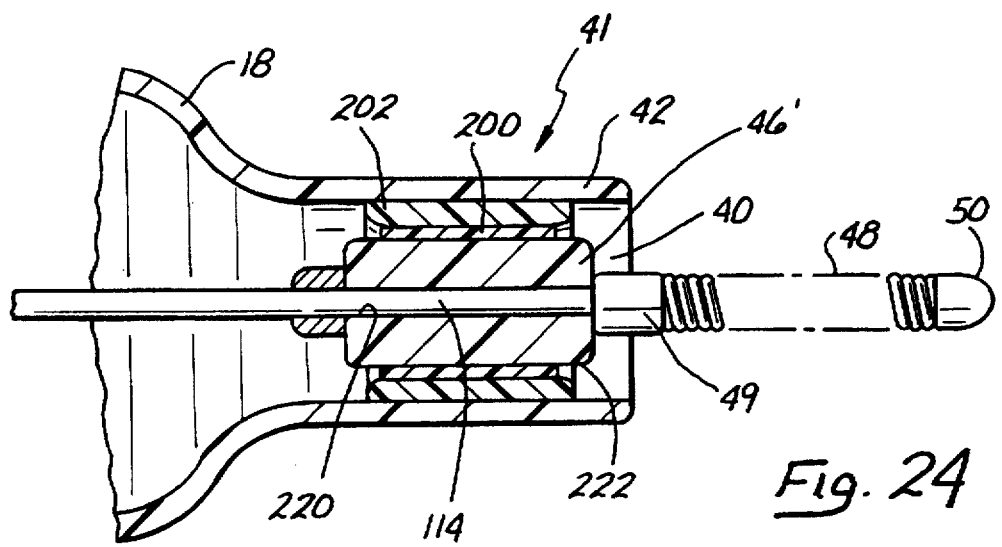

FIG. 24 shows an alternative embodiment of the present invention in which a guide wire assembly 22 as seen in FIG.

22 includes a resilient collar member 46' captured between the braze 49 and the marker 108. This resilient collar member 46' of the guide wire assembly 22 is sealingly received into a sleeve portion 42 like that seen in FIGS. 17 and 23. In other words, the sleeve portion 42 of the valving device 41 includes a tube member 200 of dimensionally stable material, such as metal or polyimide, for example. This tube member is secured into the sleeve portion with a layer 202 of adhesive. The collar member 46 may be received into the tube 200 with a close fit or with an interference fit. With the interference type of fit between the collar 46 and tube 200, the collar distorts in order to be sealingly received into the tube 200.

This combination of a resilient cylindrical collar member 46 sealingly captured radially between the hard (dimensionally stable) outer surface 114 of the guide wire and the hard (dimensionally stable) inner surface of the tube member 200 provides a very favorable tolerance to dimensional variations of the guide wire 22 and tube member 200.

Figure 25:
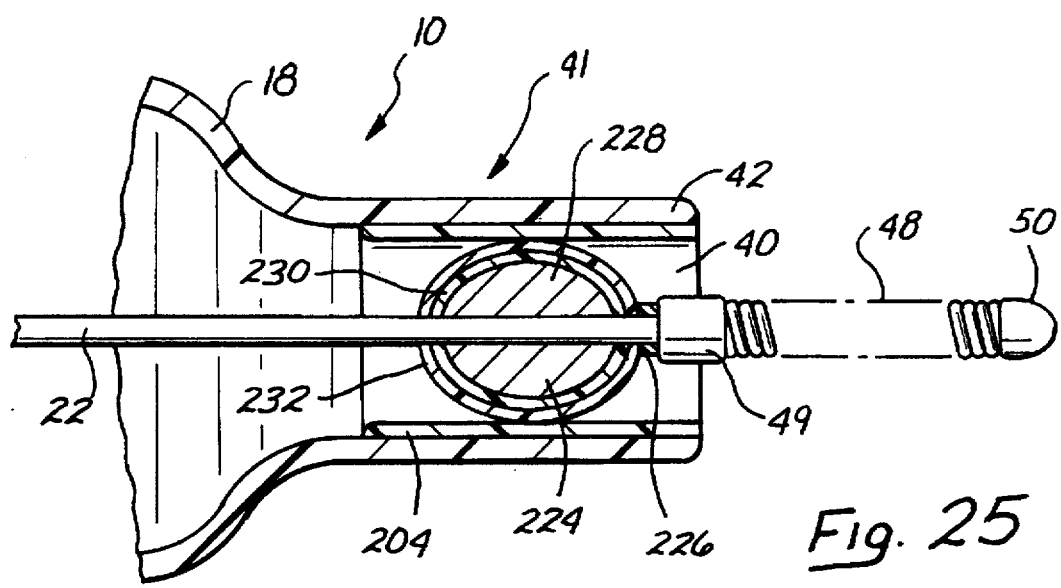

FIG. 25 depicts a particularly preferred alternative embodiment of the present invention in which a guide wire assembly 22 includes a ellipsoid-shaped, dimensionally-stable, and layered bead member 224, which is secured on the guide wire 22 slightly proximally of the braze 49. This bead member 224 inwardly may be made of metal, and may even be made of a radiopaque metal, for example, so that the bead member 224 also defines a marker for the catheter assembly 10, including guide wire assembly 22. Alternatively, a radiopaque coil or sleeve type of marker (not shown) may be provided on the guide wire 22 distally of or proximally of the bead member 224.

Carried on the bead member 224 is a first thin layer 228 of polytetrafluoroethylene, generally known as Teflon. Upon the layer 228, a second thin layer 230 of silicone is carried and defines an outer surface 232 for the bead member 224. The sleeve portion 42 of catheter assembly 10 is configured like that seen in FIG. 18, and includes a layer 204 of resilient polymeric material. More particularly, the layer 204 preferably may be a layer of resilient silicone material, or of linear low-density polyethylene. In this case, the dimensionally stable and internally hard layered bead 224 provides support for the layer of silicone 230 which sealingly engages the similar layer 204 of silicone on the inside of sleeve portion 42. This sleeve portion 42 is generally dimensionally stable, but may be subject to dimensional creep with the passage of time and with thermal cycling, as was pointed out above. The combination of the two sealingly contacting layers (204, 230) of silicone and the ellipsoid shape of the bead member 224 has been shown to provide a good sealing reliability, tolerance to dimensional variations, acceptable axial engagement and disengagement force levels, and acceptable twisting torque levels.

In fact, examples of this construction have shown very reliable sealing integrity at the valving device 41, while also showing axial engagement and disengagement forces as well as twisting torque levels for the guide wire 22 which were well below acceptable values. Still further, this embodiment of the invention provides a twisting torque level for the guide wire 22 with the valving device 41 closed which was at the very lower end of the torque measurement range for the conventional instruments which are used to test such catheter and guide wire assemblies.

Figure 26:
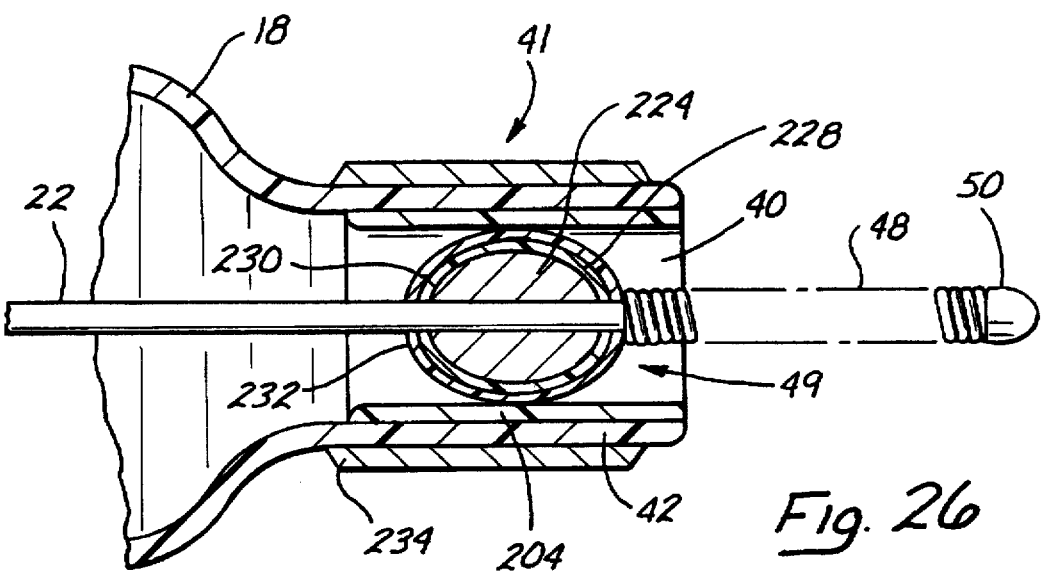

FIG. 26 shows another alternative embodiment of the invention in which a bead member 224' is formed on the guide wire 22 immediately proximally of the proximal extent of the coil 48. In fact, the bead member 224' is formed of the braze 49, and for this reason FIG. 26 includes an arrowed numeral 49 pointing to the bead member 224'. Because the bead member 224' is formed of the material of braze 49, the coil member 48 is imbedded in the bead member, and extends distally therefrom. Preferably, this bead member 224' will be formed of brazing material which is radiopaque, or which has radiopaque material added thereto, so that this bead member serves as a marker for the catheter 10. like the bead member 224 seen in FIG. 25, the bead member 224' can include layers 228 and 230 of Teflon and silicone, respectively. The outer silicone layer 230 defines a surface 232 which sealingly engages with a layer 204 of silicone material carried on the inside of sleeve portion 42. That is, the construction of the sleeve portion 42 is similar to that seen in FIGS. 18 and 25. However, the embodiment of FIG. 26 may also include an external dimensionally stable band member 234 surrounding and carried by the sleeve portion 42. This band 234 is preferably made of a material such as a metal or polyimide, which will assist in supporting the sleeve member 42, and in resisting dimensional changes thereof, for example as may otherwise occur with time and temperature cycling.

Figure 27:
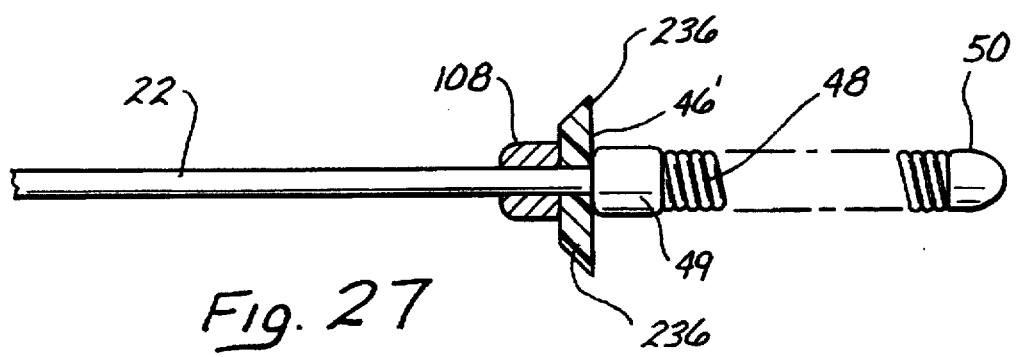
FIGS. 27 and 28 provide fragmentary cross sectional views of yet another embodiment of the invention.
Figure 28:
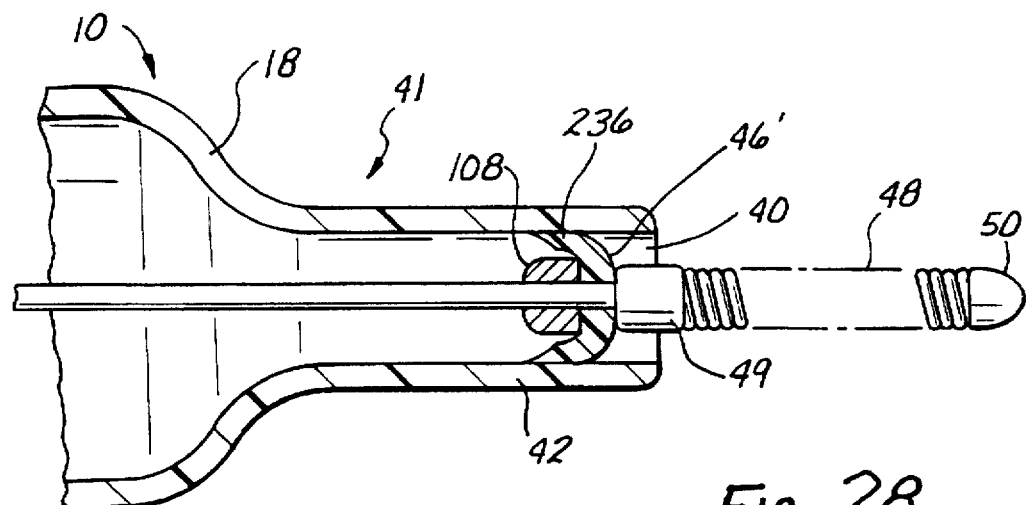

FIGS. 27 and 28 depict yet another alternative embodiment of the present invention in which a guide wire assembly 22 includes a collar member 46' trapped between the braze 49 and a marker 108. The collar member 46' is formed as a resilient disk member having an outer diameter larger than the inner diameter of the sleeve portion 42 of the catheter assembly 10. The collar member 46' also includes a tapering or conical peripheral portion, which is referenced with the numeral 236. As depicted in FIG. 27, the free or undistorted configuration of the collar member 46' is such that the peripheral portion 236 tapers axially and radially outwardly to become thinner. The axial taper of the collar member 46' is in the distal direction so that the distal side of the collar 46' is planar and the proximal side has a truncated cone shape.

FIG. 28 shows that when the guide wire 22 is moved proximally to pull the collar member 46' into the sleeve portion 42, the collar member 46' distorts to be some what cup-shaped, with the cup shape opening in the proximal direction. In other words, the collar member 46' forms a sealing cup with a sealing lip defined by peripheral portion 236 which is disposed toward the interior of balloon 18. As is well known, such a cup-type seal forms a dynamic seal which is responsive to applied fluid pressure to seal even more effectively, and which has good tolerance to variations of the surface against which a seal is to be effected. This seal structure also offers good axial and torque values. Other configurations of the collar member 46' such that it distorts from its free configuration into the sleeve portion 42 of the catheter assembly 10 to form a dynamic lip type of seal are possible, and are within the contemplation of this invention.

Figure 29:
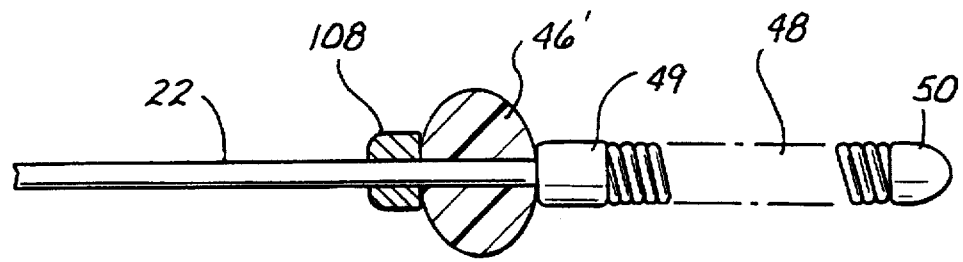
FIGS. 29 and 30 present yet another alternative embodiment of the invention.
Figure 30:
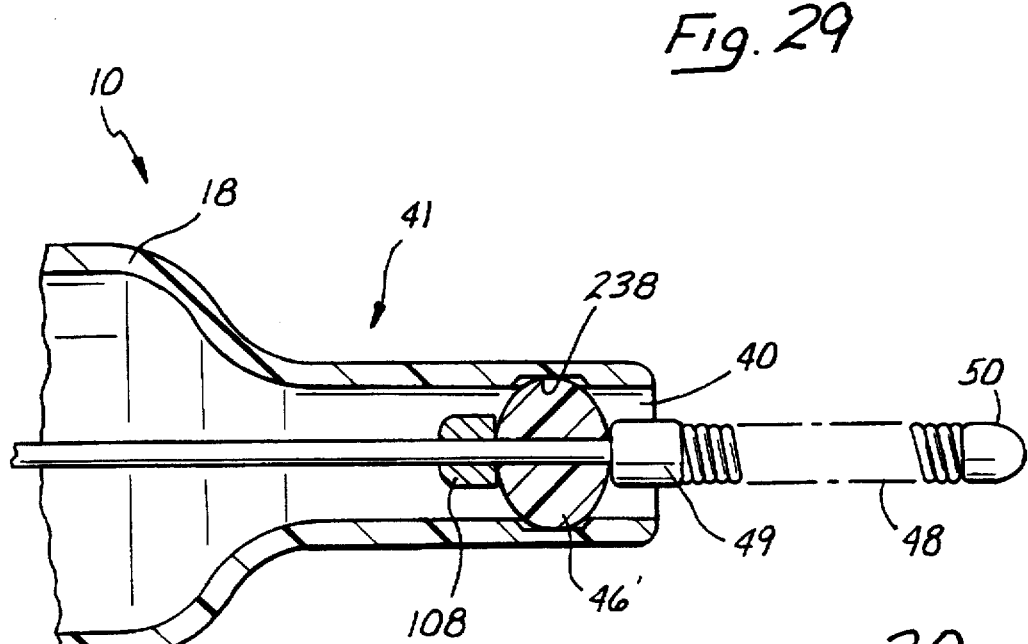

FIGS. 29 and 30 show another alternative embodiment of the present invention in which a collar member 46' is axially trapped on the guide wire 22 between the braze 49 and the marker 108. This collar member 46' is ellipsoid or oval in shape similarly to the embodiments of FIGS. 21, 23, 25, and 26. However, while the collar member 46' is a body of rotation similar to the earlier collar members, in contrast to these earlier embodiments of the invention, the ellipsoid-shaped collar member 46' of FIGS. 29 and 30 is configured with the major axis of the elliptical shape perpendicular to the axis of the wire 22. That is, the body of collar member 46' is shaped so that when viewed parallel to the axis of wire 22, it is circular, and the circular diameter is larger than its elliptical axis seen in FIG. 29. Thus, the collar member 46' has the shape of an ovoid or saucer-shape. In its free or undistorted shape, as is seen in FIG. 29, the collar member 46' has an outer diameter larger than the inner diameter of the sleeve portion 42. When the guide wire 22 is pulled proximally into the catheter 10, the collar member 46, distorts sealingly into the sleeve portion 42, viewing FIG. 30. For this reason, the collar member 46 is allowed some space between the braze 49 and marker 108 because the collar member 46 will grow a little axially as it is distorted radially into the sleeve portion 42.

Further to the above, the sleeve portion 42 is formed to internally define a shallow annular and radially-inwardly opening groove 238. The collar member 46' will distort into the sleeve portion 42, and then expand partially back toward its free or undistorted shape into the groove 238 to form a self-detenting valve structure 41 at the sleeve 42. The collar member 46' can be moved axially out of the sleeve 42 by application of force to the guide wire 22, but is not prone to falling out of the sleeve portion 42 merely from handling or manipulation of the catheter assembly 10.

Figure 31:
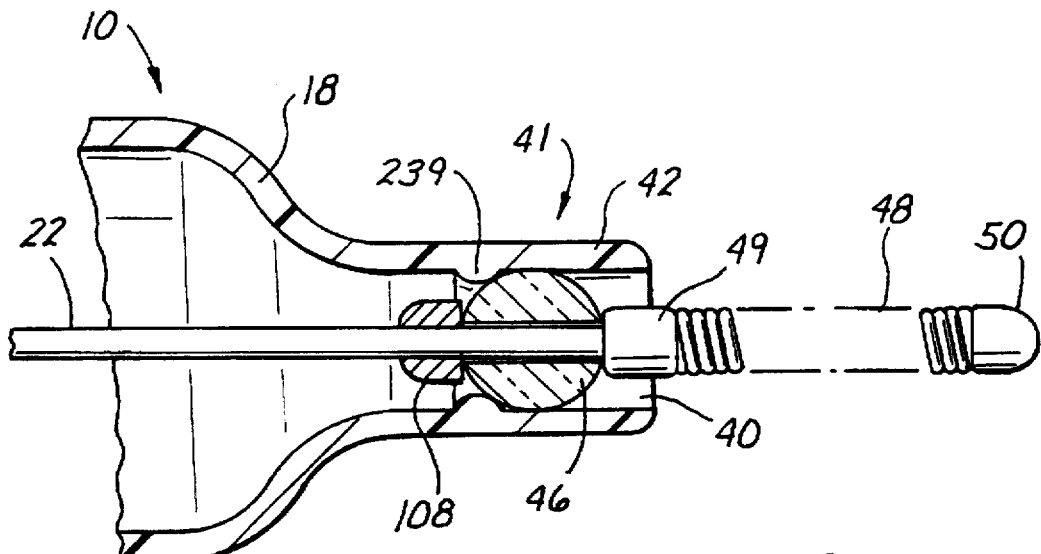
FIGS. 31 and 32 respectively present two more alternative embodiments of the invention.

FIG. 31 depicts another embodiment of the present invention in which the catheter assembly 10 is like that seen in FIG. 2, or FIG. 21, for example, and includes a resilient sleeve portion 42. Sealingly received into the sleeve portion is a collar member 46 in the shape of a pierced sphere or ball member which is carried upon the guide wire assembly 22. However, the collar member 46 surprisingly offers a heretofore unavailable level of precision, low friction engagement with the catheter shaft, uniformity of sealing fit in the sleeve 42, and sealing integrity at the sleeve 42, with attendant uniformity of selected axial engagement/disengagement force, and with low rotational torque values for torquing of the guide wire rotationally relative to the catheter shaft.

The collar member 46 is formed of $Al_2O_3$, which is synthetic ruby or synthetic sapphire gemstone. Of course, natural gemstone may also be used, if desired. Further, the gemstone need not be limited to ruby or sapphire. However, the Applicants have determined that synthetic ruby or sapphire gemstone members are available in shapes appropriate for use as collar member 46, and at a comparatively low cost. This material offers a very low coefficient of friction so that the engagement force for the collar member 46 into sleeve 42 is controllable and very predictable by precise formation of the size of the sleeve 42 relative to the size of the collar member 46. Also, the inherently low coefficient of friction of the synthetic ruby or sapphire assists in controlling this engagement force to a low level with a sufficient distortion of the resilient sleeve 42 to insure good sealing integrity at the valve device 41. Further, pierced synthetic ruby and sapphire ball members are commercially available, and are made of synthetic ruby or sapphire for use as small precision bearings in such devices as mechanical watches and instruments. These bearing ball members are available at a reasonable cost and with very high precision. For example, commercially available ball members may be had with a sphericity tolerance of only 0.000005 inch. The size tolerance for these ball members is similarly small.

With this high level of size and shape precision for the collar member 46, the sleeve portion 42 may be precision formed, and the collar member 46 will sealingly fit into this sleeve member with a precisely predictable engagement/disengagement force being provided. Further, the inner diameter of such pierced ball members is similarly precise so that a sealing but relatively rotational fit of the collar member 46 on the guide wire 22 can be achieved, if desired. Alternatively, the interface of the inner bore of the ball member 46 and the outer surface of the guide wire 22 may be provided with a layer or sleeve (not shown) of resilient material sealingly closing the space between the ball 46 and guide wire 22. For example, silicone, Nylon, and low density polyethylene may be used to coat the inner diameter of the bore in ball 46, or the congruent section of the guide wire 22, so that the two are sealingly related when the ball 46 is placed on the wire 22. These materials offer a low enough coefficient of friction, however, so that a low rotational torque value for the guide wire 22 relative to the remainder of the catheter is still provided.

The inner diameter surface of the sleeve portion 42 may also be made of or may be coated with thermoplastic or thermoset material with an enduring dimensional memory so that dimensional stability of the sleeve portion 42 is maintained. The synthetic ball member which forms the collar 46 will inherently have such a low coefficient of friction at its polished outer surface with the sleeve portion 42 that the collar member (ball) 46 may be adhesively attached to the guide wire 22, and rotational freedom of this guide wire will be provided by sliding (while still sealing) engagement of the collar member 46 within sleeve portion 42. This adhesive attachment of the collar member 46 directly to the guide wire 22 eliminates any possibility of fluid leakage between the collar and guide wire.

FIG. 31 also shows that the sleeve portion 42 may also be formed with a circumferentially and radially inwardly extending stop rib 239. This stop rib 239 is disposed proximally of the collar member (ball) 46 so that this collar member cannot be inadvertently pulled through the sleeve portion 42. The collar member 46 can be forced past the stop rib by the application of sufficient pushing or pulling force at the proximal end of the guide wire 22, so that the guide wire assembly can pass through the lumen 20 of the catheter 10. This feature of stop rib 239 at the sleeve portion 42 is of importance and greatly aids in the ability of a physician to reengage the valve ball 46 into the sleeve portion 42 without the need for fluoroscopic guidance. That is, the physician can simply feel at the guide wire 22 when the valve ball 46 has entered the sleeve portion 42, and when this valve ball encounters and is stopped from further relative proximal movement by the rib 239.

Figure 32:
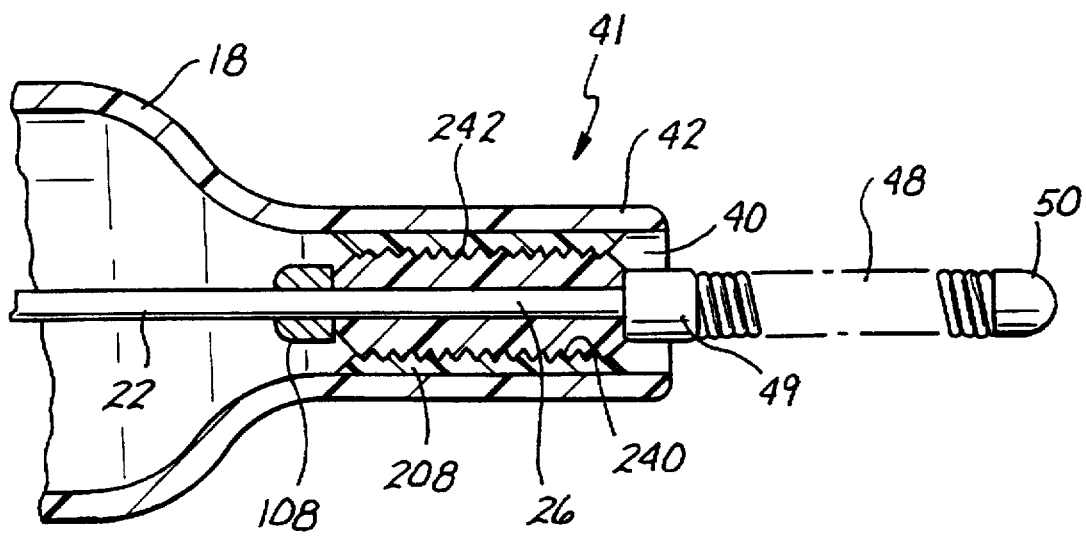

Viewing now FIG. 32, another alternative embodiment of the catheter assembly 10 is fragmentarily depicted in which the sleeve portion 42 carries internally a layer of thermoplastic material 208, like that seen in FIG. 19. However, the layer of material 208 seen in FIG. 32 is formed to include a screw thread 240. On the guide wire assembly 22, the collar member 46 is non-rotationally carried on the distal portion 26. This collar member 46 is formed with an external screw thread 242 which is threadably engageable into the thread 240 with a slight interference fit to form a sealing-tight engagement between the collar 46 and the sleeve 42. Although it is not depicted, it is apparent that a square shoulder on the collar member engaging onto a square seat of the sleeve portion, or a tapered shoulder engaging onto a tapered seat, for example, could be defined by a slightly enlarged distal portion of the collar member 46, which would seat on a distal end surface of the catheter 10. This type of sealing cooperation of the collar 46 and sleeve 42 is not depicted in the drawing Figure, and is believed not to be necessary in order to achieve a satisfactory level of sealing integrity for the balloon catheter of the present invention. The screw threads 240 and 242 may be formed with a straight triangular configuration, as depicted, and with or without a slight interference fit to effect a seal. Alternatively, the screw threads 240 and 242 may be formed with a slight taper, like pipe threads, to effect a seal as the collar 46 is threaded into the sleeve 42. Alternative thread configurations which may function satisfactorily at the valving device 41 include straight or tapered acme-form threads, and multistart threads.

The embodiment of the present invention depicted in FIG. 32 has a particular advantage in that a disengagement apparatus, like that seen in FIGS. 14 and 15, is not required for the catheter assembly 10 including guide wire assembly 22. In other words, the physician can rotate the guide wire as necessary (using a torquer if desired) to effect steering of the catheter assembly along a vascular pathway, with the collar 46 threadably received in the sleeve 42. A sufficient extent of threaded engagement is provided that the collar member 46 is not inadvertently unthreaded from the sleeve 42.

This threaded engagement of the collar 46 into the sleeve 42 at the distal end of the catheter assembly 10 has the additional advantage of insuring the physician that manipulations of the catheter assembly, such as pushing this assembly along a guide catheter or through a tight lesion, for example, will not inadvertently cause the collar 46 to disengage from the sleeve 42. When the physician is ready to disengage the collar 46 from within the sleeve 42, the torquer 32 may be used to make a sufficient number of rotations to the guide wire assembly 22 relative to the remainder of the catheter and in the direction to unscrew the collar 46 distally from the sleeve 42. Once this disengagement of the catheter assembly 10 from the guide wire assembly 22 is accomplished, the physician will be able to feel the relatively free relative axial mobility of these two assemblies. A catheter exchange, if necessary, can then be accomplished as described above. The replacement catheter assembly will need to be configured with a matching internally-threaded sleeve portion 42 to sealingly cooperate with the collar portion 46 of the guide wire assembly 22.

Figure 33:
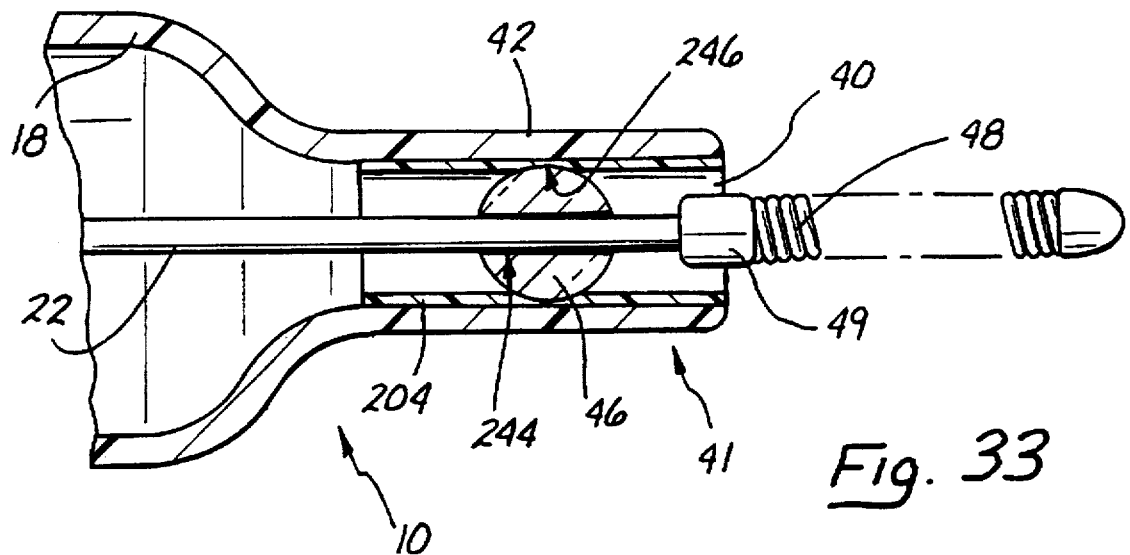
FIGS. 33 and 34 respectively depict two additional alternative embodiments of the invention, which are similar in several respects both to one another and to the embodiments of FIGS. 18 and 25, and also to the embodiment of FIG. 31.

FIG. 33 depicts yet another alternative embodiment of the present invention, which is particularly preferred. This embodiment includes a sleeve portion 42 of valving device 41, which sleeve portion 42 includes a layer 204 of material which is at least somewhat elastic or resilient. As pointed out in connection with the description of FIGS. 18, and 25, this layer 204 of elastic or resilient material may be formed of silicone or of linear low-density polyethylene, for example. On the guide wire assembly 22 is adhesively and sealingly secured a collar member 46 of synthetic ruby or sapphire, as was described above with respect to FIG. 31. That is, an adhesive, as is indicated by the arrow 244 secures and seals the spherical collar 46 to the wire 22. The undistorted inner diameter of the elastic or resilient layer 204 is less than the outer diameter of the collar (ball) 46 by a selected amount.

Accordingly, the collar 46, when forcefully drawn into the sleeve portion 42 causes an elastic deformation of the layer 204, as is indicated by the arrow 246. Preferably, the deformation of the material of layer 204 is elastic deformation, and is maintained well below the level of deformation necessary for plastic deformation of this material. For example, with linear low-density polyethylene for the layer 204, a deformation of about 37 percent is necessary before the material deforms plastically (i.e., permanently). Accordingly, the deformation 246 at the interface of the collar (ball) 46 and the layer 204 of elastic or resilient material is maintained at a level of about 6 percent to about 8 percent. This level of elastic deformation of the elastic or resilient layer 204 is only a fractional portion of the deformation which would be necessary to effect permanent deformation of the layer 204 and is sufficiently low that the collar (ball 46) may easily be turned within sleeve 42 with a low required torque while still maintaining a good seal. That is, the ball 46 may be rotated within sleeve 42 with a low torque value which prevents wrapping of the balloon 18 about wire 22, while still maintaining a very good sealing integrity at the interface of the ball 46 and sleeve 42. Also, the collar (ball) 46 can easily be disengaged from and reengaged with the sleeve portion 42. Tests of this embodiment of the invention have shown good sealing integrity when subjected to an internal pressure of up to 25 atmospheres, even with repeated engagements and disengagements of the ball 46 into the sleeve portion 42. Mathematical analysis further shows that this embodiment of the present invention should have good sealing integrity with an internal pressures up to 95 atmospheres, or more. Because the expected inflation pressure for the dilatation balloon 18 is only 15 to 25 atmospheres, the surprising and unexpected combination of excellent sealing integrity and low disengagement/reengagement forces, along with low guide wire torque values achieved by the use of the synthetic gemstone collar (ball) 46, and a layer of elastic or resilient material 204 within the sleeve portion 42 is well beyond the requirements for the catheter 10.

Figure 34:
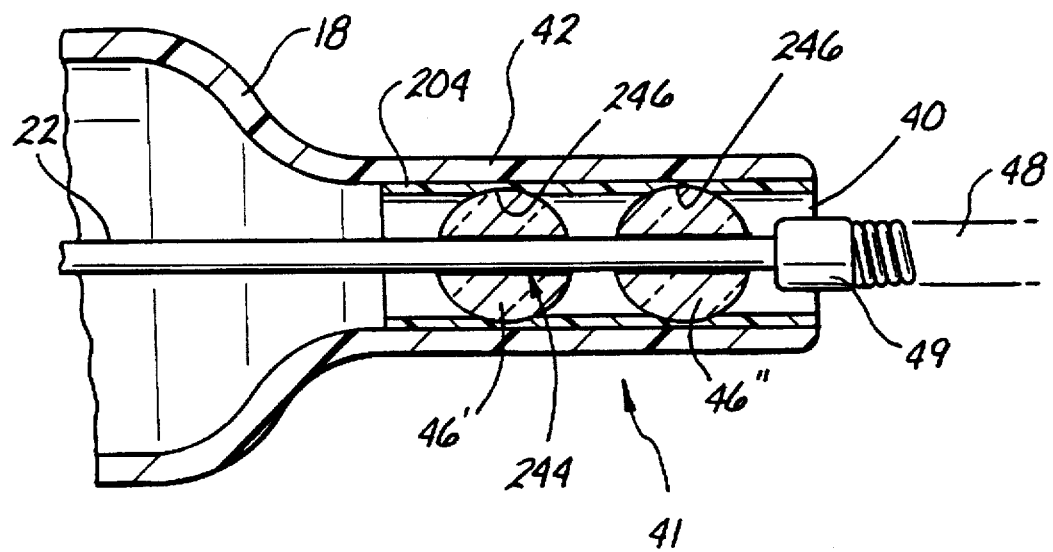

FIG. 34 depicts yet another alternative embodiment of the present invention, which embodiment also has similarities to those embodiments depicted in FIGS. 18, 25, 31, and 33. In the embodiment shown in FIG. 34, the sleeve portion 42 internally carries a layer 204 of elastic or resilient material. However, in order to achieve a higher engagement/disengagement force into and out of the sleeve portion 42 for the collar 46, this collar is made with at least two of the pierced synthetic gemstone balls (referred to as 46' and 46") arranged in series and adjacent to one another. The proximal one (46') of the pair of gemstone balls is adhesively secured to the guide wire 22 by a layer of adhesive 244, as was explained with reference to FIG. 33. However, the distal one (46") of the two gemstone balls is axially positioned with free relative rotation on the guide wire 22 merely by the adjacent braze 49 on one side, and by the other adhesively-secured ball 46' on the other side of the ball 46".

Both of the balls 46', 46", elastically distort (arrow 246) the layer 204 of elastic or resilient material. However, the sealing integrity of the proximal ball 46' is so good that the distal ball 46" is not needed for additional sealing security. For this reason, no effort is made to seal the bore of the ball 46" with the guide wire 22. The second and distal ball 46" is provided in order to increase the level of axial force required on guide wire 22 to effect engagement and disengagement of the collar portion 46 (balls 46' and 46") of the valving device 41, while maintaining a desirably low torquing value for the guide wire 22. This latter objective is accomplished because the distal ball 46" contributes to a desired increase in the axial force, but is freely rotational on the guide wire 22 so that torque values for rotation of the guide wire 22 are not increased by the second ball member 46". Also, this feature provides the desired level of tactile feel for engagement and disengagement of the collar 46 into sleeve 42, while preserving the greatly reduced or eliminated wrapping of the balloon about the guide wire 22 when the guide wire is torqued relative to the catheter shaft. Thus, when the valving device 41 is closed by forceful engagement of the balls 46' and 46" into the sleeve portion 42, torquing the guide wire 22 slides the ball 46' at its sealing engagement with the layer 204. The guide wire 22 rotates freely within the distal ball 46" and the torquing level for the catheter 10 is about the same as the embodiment shown in FIG. 33.

Thus, the apparatus of the present invention provides an exchangeable integrated-wire balloon catheter that can be positioned within a vascular pathway by a single vascular physician. Because the apparatus of the present invention provides the maneuverability of a fixed-wire dilatation catheter coupled with the benefits of a catheter of ultra-low profile, it can be quickly and easily maneuvered into position across lesions that are critically narrowed and which are shaped irregularly. Following expansion of the balloon and dilation of the lesion the catheter of the present invention can be disengaged from the distal end of its guide wire and retracted back from the lesion to allow the physician to visualize blood flow while retaining guide wire access across the lesion. If necessary, the physician can advance the balloon and reengage the distal end of the guide wire to reseal the balloon for purposes of re-inflation. Alternatively, while leaving the guide wire in place the physician can completely remove and replace the balloon catheter with one having alternative dimensions which, in turn, can be sealingly engaged with the distal end of the guide wire for inflation purposes or a conventional over-the-wire catheter may be advanced along the wire. Lastly, in cases of acute re-closure the guide wire of the present invention can be utilized to direct a perfusion catheter into position. The guide wire may also be removed, reengaged or replaced.

In closing it is to be understood that the embodiments of the invention disclosed herein are illustrative of the principals of the invention and that other modifications may be employed which are within the scope thereof. Thus, by way of example, but not of limitation, the resilient sleeve may be configured to extend into the interior of the dilatation balloon, as opposed to the outwardly-extending configuration of the releasable sealing means illustrated. Any of the modifications described herein may also be applied to an embolectomy balloon catheter in accordance with the present invention. Accordingly, the present invention is not limited to that precisely as shown and described in the specification.

According to further aspects of the present invention, which are set forth in the following paragraphs, the invention may be seen to include and to comprise: a balloon catheter and guide wire combination including a flexible, elongate, small-diameter guide wire having a distal end valving portion of comparatively enlarged diameter, and a highly-flexible distal end portion joining with the remainder of the guide wire; a flexible elongated tubular shaft having a proximal end and a distal end portion defining a distal end and at least one axially-extending fluid-conducting through lumen adapted to receive the guide wire therethrough; the distal end portion of the tubular shaft being adapted to sealingly cooperate with the enlarged-diameter distal end valving portion of the guide wire in a selected position of the latter to distally close the lumen; and the tubular shaft at the distal end portion thereof including an expansible balloon member having a proximal end and a distal end and defining a portion of the through lumen, the proximal end of the balloon member attaching to the remainder of the tubular shaft adjacent to a distal end thereof and defining the distal end portion for the shaft.

Also, the invention may be seen to include the subject matter set forth in the paragraph above, and further including the balloon catheter wherein the through lumen is of a size sufficient to pass the enlarged-diameter distal end valving portion of the guide wire.

Still further, the present invention may be seen to include the subject matter set forth in the above paragraphs, and further wherein the elongated tubular shaft and the expandable balloon are formed of resilient polymeric material.

Also, the balloon catheter of the above paragraphs may include the polymeric material of the elongate tubular shaft being selected from the group comprising homopolymers and copolymers of: polyvinylchloride, polyethylene, polyolefin, fluoropolymer, polyamide, polyester, polyimide, and polypropylene.

Additionally, the balloon catheter described in the paragraphs above may include the polymeric material of the expandable balloon being selected from the group of materials including: latex, kraton and silicone.

In yet another aspect, the present invention may include the balloon catheter as described in the paragraphs above, and wherein the catheter further includes a wrapping of filamentary material about one of the proximal end and the distal end of the balloon.

Still further, the present balloon catheter may be seen to further include a coating of binding material over the wrapping of filamentary material.

Another aspect of the present balloon catheter according to the above paragraphs provides the coating of binding material including a urethane material.

According to a comparatively broad aspect of the present invention, the balloon catheter described in the paragraphs above may include the guide wire including an elongate wirelike portion extending between a proximal end thereof and the enlarged-diameter distal end valving portion thereof, and a distal highly-flexible coil portion disposed distally of the enlarged-diameter distal end valving portion, the wirelike portion and the distal end highly-flexible coil portion being joined to one another to define a braze joint, and the tubular shaft including a distally-extending circumferential portion which is radially congruent with the braze joint to shield the latter when the enlarged-diameter distal end valving portion of the guide wire is received sealingly into the distal end portion of the tubular shaft.

The balloon catheter set forth in the paragraph immediately above may include the distal end portion of the tubular shaft including one of: a resilient sleeve member extending from the distal end of the balloon and attached to the distal end of the tubular shaft, the sleeve member being dimensioned to slidingly and sealingly receive the enlarged-diameter distal end valving portion of the guide wire; a resilient sleeve member including a proximal portion received within the elongate shaft at a distal end portion of the latter, the elongate sleeve member also including a distal portion extending distally beyond the shaft and being dimensioned to sealingly receive the enlarged-diameter valving portion of the guide wire; and a dimensionally stable sleeve member received within or circumscribing the distal end portion of the catheter shaft distally of the balloon to dimensionally stabilize the distal portion.

Still further, the balloon catheter described above may include the distal end portion of the tubular shaft including an internal layer of elastic or resilient material which is dimensionally conformal to and sealingly engageable with the enlarged-diameter distal end valving portion of the guide wire.

Another aspect of the balloon catheter of the above paragraphs includes the enlarged-diameter distal end valving portion of the guide wire including a collar member carried upon the guide wire, the collar member having a larger diameter than the remainder of the guide wire proximally and distally thereof; and the collar member having a shape selected from the group including: cylindrical, conical, ellipsoid, disklike, spherical, ovoid, and saucer-shape.

Still further, the balloon catheter described above may include the collar member being shape-retaining and dimensionally-stable in character.

As described above, the balloon catheter of the preceding paragraphs may include the collar member being of yieldably shape-retaining elastic character to vary in dimension in response to forces applied thereto, the collar member in its free undistorted condition defining an inner diameter smaller than the outer diameter of the guide wire congruent with the collar member, and the collar member being elastically expanded onto the guide wire to sealingly prevent leakage of inflation fluid from the balloon between the collar member and the guide wire; and the collar member in its free undistorted condition defining an outer diameter which is larger than an inner diameter of the tubular shaft distal end portion, the collar member being distorted sealingly into the distal end portion of the tubular shaft distal end portion.

The balloon catheter described above may include the collar member further carrying a coating selected from the group including: polytetrafluoroethylene and silicone.

This balloon catheter may include a torquer for use to rotate the guide wire of a balloon catheter and guide wire combination, the torquer including a collet portion defining a through passage passing the guide wire, the collet member including a plurality of jaw features cooperatively engageable with the guide wire to transmit torque thereto, means for selectively engaging and disengaging the jaw features from the guide wire, and a guide member received in the through passage of the collet member and centering the guide wire relative to the plurality of cooperable jaw features preparatory for engagement therebetween.

This torquer may include the guide member including a funnellike entrance portion disposed distally of the catheter for guiding a proximal end of the guide wire into the jaw features, a cylindrical guide bore portion located immediately distally of the plurality of jaw features, the cylindrical guide bore portion being sized to closely pass the guide wire and to center the latter relative to the plurality of jaw features, and the guide member further including an elongate tapering guide bore portion intermediate of the funnellike portion and the cylindrical guide portion.

According to another broad aspect of the present invention, the balloon catheter and guide wire combination may comprise: a flexible, elongate, small-diameter guide wire having a wirelike proximal portion, and a distal end valving portion of comparatively enlarged diameter; a flexible elongated tubular shaft having a proximal end, a distal end, and at least one axially-extending fluid-conducting inflation lumen adapted to receive the guide wire therethrough; an expansible balloon member having a proximal end and a distal end, the balloon member including a distal end orifice, and cooperable sealing means at the distal end orifice for sealingly cooperating with the enlarged-diameter distal end valving portion of the guide wire to selectively open and close fluid communication through the distal end orifice; and the balloon catheter and guide wire combination further including proximal disengager means for selectively moving the guide wire axially relatively to the tubular shaft to engage and disengage the enlarged-diameter distal end valving portion of the guide wire with the cooperable sealing means.

This combination of balloon catheter and guide wire as described in the paragraph above may include also the proximal disengager means including a body carried upon the guide wire proximally of the tubular shaft member, the body defining a through bore movably passing the guide wire, and means for frictionally engaging the guide wire for axial movement in unison with the body relative to the tubular shaft.

Still further, this catheter and guide wire combination may include the disengager body being of shape-retaining yieldably elastic character, the means for engaging the guide wire including the body outwardly defining grip surfaces for manually effecting distortion of the body into frictional engagement at the through bore with the guide wire.

Additionally, this combination of catheter and guide wire may include the proximal disengager means including a body juxtaposed with a proximal portion of the guide wire, the body including a through bore passing the guide wire, and a pair of confronting gripper members receiving the guide wire therebetween, the gripper members inwardly defining a surface portion for frictional engagement with the guide wire and outwardly defining a manually-engageable surface portion for receiving manual force to effect frictional engagement of the gripper members with the guide wire.

The combination described in the paragraphs above may also include a member carrying the disengager body for axial relative movement with or relative to the guide wire, and further including yieldable resilient means extending between the member and the body for yieldably urging the latter proximally to a first position preparatory to distal movement together of both the body and the gripped guide wire to a second position decoupling the enlarged-diameter distal end valving portion of the guide wire from sealing cooperation with the tubular shaft.

Still further, the present invention includes a balloon catheter assembly, the balloon catheter assembly being usable with an elongate guide wire assembly having an enlarged distal end valving portion, the balloon catheter assembly including an elongate catheter shaft carrying an expansible balloon adjacent to a distal end thereof and defining a dual-purpose lumen both for communicating inflation fluid to the balloon and for passing the guide wire assembly, a distal orifice having an inner diameter and communicating outwardly of the balloon, and selective sealing means cooperable with the enlarged distal end valving portion of the guide wire assembly for in cooperation with the enlarged-diameter distal end valving portion of the guide wire assembly sealingly closing the distal orifice to retain pressurized inflation fluid within the balloon and for allowing selective opening of the distal orifice in response to axial relative movement of the guide wire assembly, the selective sealing means including one of a dimensionally-stable means isolated from or resistive to dimensional change of the balloon at the distal orifice for reliably effecting sealingly cooperating with the enlarged distal end portion of the guide wire to sealingly close the distal orifice, or dimensionally conformal means for reliably effecting sealing cooperation with the enlarged-diameter distal end valving portion of the guide wire assembly despite dimensional change of the balloon at the distal orifice.

The balloon catheter assembly described immediately above may include the dimensionally-stable means including a dimensionally-stable tube member disposed at the distal orifice, the dimensionally stable tube means defining an inner diameter which is either sized to sealingly receive and cooperate with the enlarged diameter distal end valving portion of the guide wire assembly, or which receives a portion of the distal orifice and is secured thereto to stabilize the inner diameter dimension of the distal orifice for sealing cooperation with the enlarged-diameter distal end valving portion of the guide wire assembly.

Also, the balloon catheter assembly as described in the paragraphs immediately above may include the dimensionally-stable tube member being secured at the distal orifice either within the distal orifice by a surrounding layer of adhesive, or around the distal orifice by a layer of adhesive or a material bond within the tube member.

The balloon catheter assembly of the above paragraphs may also include the dimensionally-stable tube member being fabricated of a material selected from the group including: metals, thermoplastic and thermoset polymers, and polyimide.

This balloon catheter assembly described above may also have the layer of thermoplastic material and the enlarged diameter distal end portion of the guide wire each define one of a pair of cooperative screw thread surfaces, the screw thread surfaces threadably and sealingly engaging one another when the enlarged-diameter distal end valving portion of the guide wire is sealingly cooperating with the selective sealing means.

Still further, this balloon catheter assembly of the paragraphs above may include the distal orifice being defined by a distally extending sleeve portion of the balloon, the dimensionally-stable means including a distally extending tube member having a proximal portion sealingly received in the sleeve, and a distal portion disposed distally of the sleeve, the distal portion of the tube member defining a bore dimensioned for sealing cooperation with the enlarged-diameter distal end portion of the guide wire, and the distal portion of the tube member being isolated from dimensional changes of the sleeve portion of the balloon.

The balloon catheter assembly described in the paragraphs above may also include the selective sealing means including dimensionally-conformal and shape-retaining yieldable elastic sealing means compensatory for dimensional change of the balloon at the distal orifice for sealingly cooperating with the enlarged distal end valving portion of the guide wire assembly, thereby to sealingly close the distal orifice despite dimensional change of the balloon at the distal orifice thereof, and wherein the elastic sealing means including a circumferential and axially extending layer of elastic material carried within the distal orifice for sealing cooperation with the enlarged distal end portion of the guide wire.

This balloon catheter as described above also may have the elastic layer formed of a material selected from the group including silicone, and linear low-density polyethylene.

Still further to the above, the balloon catheter described immediately above may include the layer of elastic material being elastically strained by entrance into the distal orifice of the enlarged-diameter distal end valving portion of the guide wire assembly, the elastic straining of the elastic material being limited to a fractional portion of the strain level which would effect plastic deformation of the elastic material, thereby to preserve sealing engagement of the enlarged-diameter distal end valving portion of the guide wire assembly with the elastic material at the distal end orifice despite repeated sealing engagement and disengagement therewith.

According to another aspect of the present invention, the invention may include an elongate guide wire assembly including an enlarged-diameter distal end valving portion, the guide wire assembly being for use with a balloon catheter assembly which includes an elongate catheter shaft carrying an expansible balloon adjacent to a distal end thereof and defining a dual-purpose lumen both for communicating inflation fluid to the balloon and for passing the guide wire assembly, the balloon catheter assembly also including a distal orifice communicating outwardly of the balloon and selective sealing means at the distal orifice for sealing cooperation with the enlarged-diameter distal end valving portion of the guide wire assembly to close the distal orifice, the elongate guide wire assembly comprising: an elongate wirelike shaft portion; a highly-flexible distal end portion joined to the elongate wirelike shaft portion; and a collar member carried upon the wirelike shaft portion proximally adjacent to the highly-flexible distal end portion to define the enlarged-diameter distal end valving portion thereof.

This guide wire assembly described in the paragraph immediately above may include the guide wire assembly including means securing the collar axially relative to the wirelike shaft portion, the securing means being selected from the group including: adhesive material securing the collar member to the wirelike shaft portion; the collar member being formed in compression upon and bonding to the wirelike shaft portion to secure thereto; the collar member being shrunk from a previously enlarged-diameter size onto the wirelike shaft portion to compressively grip the shaft portion; a fine-dimension tubular member which with a congruent section of the wire-like shaft portion cooperatively defines essentially a zero-clearance radial fit therebetween thereby to prevent leakage of pressurized inflation fluid from the balloon through the clearance; a bandlike member physically securing to the wirelike shaft portion and axially confronting the collar member to position the latter relative to the shaft portion with the bandlike member defining a chamfer surface disposed proximally to guide entrance of the collar member and the bandlike member into the distal orifice; and the bandlike member being formed of radiopaque material so that the bandlike member serves as a marker for the position of the guide wire.

This guide wire assembly described above may include the collar member being of a shape selected from the group including: disklike, spherical, ellipsoid, ovoid, conical, and saucer-shape.

Still further, the guide wire assembly described above may have the collar member formed of a material selected from the group including: metal, polymers, elastomers, and gemstone including synthetic sapphire and ruby.

Also, this guide wire assembly, as described, may include the collar member including a pair of pierced synthetic gemstone beads carried on the wirelike shaft portion, a proximal one of the beads being adhesively secured to the shaft portion of the guide wire assembly, and the distal one of the beads being freely relatively rotational on the shaft portion.

Further to the above, this guide wire assembly of the paragraphs above may include the collar member carrying outwardly thereon a coating of material selected from the group including: polytetrafluoroethylene, and silicone.

Finally, this guide wire assembly may also include the collar member carrying outwardly thereon both a coating of polytetrafluoroethylene, and a coating of silicone over the coating of polytetrafluoroethylene.

We claim:

1. A torquer for use to rotate the guide wire of a balloon catheter and guide wire combination, said torquer including a collet portion defining a through passage passing said guide wire, said collet member including a plurality of jaw features cooperatively engageable with said guidewire to transmit torque thereto, threaded ring member disposed about the jaw features which upon tightening or loosening selectively engages and disengages said jaw features from said guide wire, and a guide member received in said through passage of said collet member and centering said guide wire relative to said plurality of cooperable jaw features preparatory for engagement therebetween.

2. The torquer of claim 1 wherein said guide member includes a funnel-like portion disposed distally of said catheter for guiding a proximal end of said guide wire into said jaw features.

3. The torquer of claim 2 wherein said guide member further includes a cylindrical guide portion located immediately distally of said plurality of jaw features, said cylindrical guide portion being sized to closely pass said guide wire and to center the latter relative to said plurality of jaw features.

4. The torquer of claim 3 wherein said guide member further includes an elongate tapering guide portion intermediate of said funnel-like portion and said cylindrical guide portion.

5. The torquer of claim 1 wherein said means for selectively engaging and disengaging said plurality of jaw features from said guide wire includes means for selectively contracting said collet member at said jaw portions.

6. The torquer of claim 5 wherein said selective contracting means includes said collet member defining an enlarged axially-tapering portion, and a housing receiving said collet member, said housing including a pair of axially-tapering and selectively axially relatively movable opposed surface portions which are engageable on opposite axial sides of said enlarged portion of said collet to squeeze the latter therebetween, thereby contracting said jaw portions cooperatively into engagement with said guide wire.

* * * * *